United States Patent
Kohan et al.

(10) Patent No.: US 8,275,850 B2
(45) Date of Patent: Sep. 25, 2012

(54) MULTI-SOURCE LONGITUDINAL PATIENT-LEVEL DATA ENCRYPTION PROCESS

(75) Inventors: Mark E. Kohan, Downingtown, PA (US); Clinton J. Wolfe, Malvern, PA (US)

(73) Assignee: IMS Software Services Ltd., Plymouth Meeting, PA (US)

( * ) Notice: Subject to any disclaimer, the term of this patent is extended or adjusted under 35 U.S.C. 154(b) by 653 days.

(21) Appl. No.: 11/122,589

(22) Filed: May 5, 2005

(65) Prior Publication Data

US 2005/0268094 A1 Dec. 1, 2005

Related U.S. Application Data

(60) Provisional application No. 60/568,455, filed on May 5, 2004, provisional application No. 60/572,161, filed on May 17, 2004, provisional application No. 60/571,962, filed on May 17, 2004, provisional application No. 60/572,064, filed on May 17, 2004, provisional application No. 60/572,264, filed on May 17, 2004.

(51) Int. Cl.
    *G06F 15/167* (2006.01)
(52) U.S. Cl. ........................................... 709/212
(58) Field of Classification Search .................. 713/165; 709/212
    See application file for complete search history.

(56) References Cited

U.S. PATENT DOCUMENTS

| | | | |
|---|---|---|---|
| 5,084,828 A | 1/1992 | Kaufman et al. | 364/479 |
| 5,331,544 A | 7/1994 | Lu et al. | 364/401 |
| 5,365,589 A | 11/1994 | Gutowitz | |
| 5,420,786 A | 5/1995 | Felthauser et al. | 364/401 |
| 5,490,060 A | 2/1996 | Malec et al. | 364/401 |
| 5,499,293 A | 3/1996 | Behram et al. | |
| 5,519,607 A | 5/1996 | Tawil | 364/401 |
| 5,606,610 A | 2/1997 | Johansson | |
| 5,666,492 A | 9/1997 | Rhodes et al. | 705/3 |

(Continued)

FOREIGN PATENT DOCUMENTS

JP          2000324094          11/2000

(Continued)

OTHER PUBLICATIONS

U.S. Appl. No. 11/122,565, filed May 5, 2005.

(Continued)

*Primary Examiner* — Kambiz Zand
*Assistant Examiner* — Stephen Sanders
(74) *Attorney, Agent, or Firm* — Fish & Richardson P.C.

(57) ABSTRACT

Systems and processes for assembling de-identified patient healthcare data records in a longitudinal database are provided. The systems and processes may be implemented over multiple data suppliers and common database facilities while ensuring patient privacy. At the data supplier locations, patient-identifying attributes in the data records are placed in standard format and then doubly encrypted using a pair of encryption keys before transmission to a common database facility. The pair of encryption keys includes a key specific to the data supplier and a key specific to the common database facility. At the common database facility, the encryption specific to the data supplier is removed, so that multi-sourced data records have only the common database encryption. Without direct access to patient identifying-information, the encrypted data records are assigned dummy labels or tags by which the data records can be longitudinally linked in the database. The tags are assigned based on statistical matching of the values of a select set of encrypted data attributes with a reference database of tags and associated encrypted data attribute values.

24 Claims, 23 Drawing Sheets

U.S. PATENT DOCUMENTS

| | | | |
|---|---|---|---|
| 5,737,539 A | 4/1998 | Edelson et al. | 395/203 |
| 5,758,095 A | 5/1998 | Albaum et al. | 395/202 |
| 5,758,147 A | 5/1998 | Chen et al. | 395/606 |
| 5,781,893 A | 7/1998 | Felthauser et al. | 705/210 |
| 5,845,255 A | 12/1998 | Mayaud | 705/3 |
| 5,991,758 A | 11/1999 | Ellard | |
| 6,061,658 A | 5/2000 | Chou et al. | 705/10 |
| 6,249,769 B1 | 6/2001 | Ruffin et al. | 705/7 |
| 6,285,983 B1 | 9/2001 | Jenkins | 705/10 |
| 6,397,224 B1* | 5/2002 | Zubeldia et al. | 707/102 |
| 6,430,292 B1 | 8/2002 | Ito et al. | |
| 6,654,724 B1 | 11/2003 | Rubin et al. | |
| 6,732,113 B1* | 5/2004 | Ober et al. | 707/102 |
| 6,874,085 B1 | 3/2005 | Koo et al. | |
| 6,988,075 B1 | 1/2006 | Hacker | |
| 7,127,432 B2 | 10/2006 | Rubin et al. | |
| 7,143,289 B2* | 11/2006 | Denning et al. | 713/168 |
| 7,260,215 B2* | 8/2007 | Troyansky et al. | 380/28 |
| 7,376,677 B2* | 5/2008 | Ober et al. | 707/204 |
| 2001/0019614 A1 | 9/2001 | Madoukh | |
| 2002/0073099 A1 | 6/2002 | Gilbert et al. | |
| 2002/0073138 A1* | 6/2002 | Gilbert et al. | 709/201 |
| 2002/0083192 A1 | 6/2002 | Alisuag | |
| 2002/0128860 A1 | 9/2002 | Leveque et al. | |
| 2002/0136407 A1* | 9/2002 | Denning et al. | 380/258 |
| 2002/0165736 A1 | 11/2002 | Tolle et al. | |
| 2002/0193905 A1 | 12/2002 | Davison et al. | |
| 2002/0194024 A1 | 12/2002 | Fleinshmidt | |
| 2003/0021417 A1 | 1/2003 | Vasic et al. | |
| 2003/0039362 A1 | 2/2003 | Califano et al. | |
| 2003/0041241 A1 | 2/2003 | Saito | |
| 2004/0117215 A1 | 6/2004 | Marchosky | |
| 2004/0193905 A1 | 9/2004 | Lirov et al. | |
| 2005/0147246 A1 | 7/2005 | Agrawal et al. | |
| 2005/0216313 A1 | 9/2005 | Claud et al. | |
| 2005/0234909 A1 | 10/2005 | Bade et al. | |
| 2005/0256740 A1 | 11/2005 | Kohan et al. | |
| 2005/0256741 A1 | 11/2005 | Kohan et al. | |
| 2005/0256742 A1 | 11/2005 | Kohan et al. | |
| 2005/0268094 A1 | 12/2005 | Kohan et al. | |
| 2005/0288964 A1 | 12/2005 | Lutzen et al. | |
| 2006/0178892 A1* | 8/2006 | Oon | 705/1 |

FOREIGN PATENT DOCUMENTS

| | | |
|---|---|---|
| JP | 2002032473 | 1/2002 |
| JP | 2003005645 | 1/2003 |
| JP | 2003173376 | 6/2003 |
| WO | WO01/41353 | 6/2001 |
| WO | WO02/063823 | 8/2002 |
| WO | WO 02/063823 | 8/2002 |
| WO | WO 01/41353 | 10/2003 |

OTHER PUBLICATIONS

U.S. Appl. No. 11/122,581, filed May 5, 2005.

Tsukagoshi, Noboru, "Ubiquitous computing and distribution system", *Magazine of "Logistic System"*, Japan Logistics System Institute, Jan. 30, 2004, 13(2): 32-38.

Non-Final Rejection mailed Apr. 27, 2009 for U.S. Appl. No. 11/122,564.

Non-Final Rejection mailed Apr. 23, 2009 for U.S. Appl. No. 11/122,565.

Amendment and Response filed Oct. 23, 2009 for U.S. Appl. No. 11/122,565.

Final Rejection mailed Nov. 12, 2009 for U.S. Appl. No. 11/122,565.

Notice of Appeal filed May 12, 2010 for U.S. Appl. No. 11/122,565.

Non-Final Rejection mailed Dec. 31, 2008 for U.S. Appl. No. 11/122,581.

Amendment and Response filed May 29, 2009 for U.S. Appl. No. 11/122,581.

Final Rejection mailed Sep. 2, 2009 for U.S. Appl. No. 11/122,581.

Amendment and Response and Request for Continued Examination (RCE) filed Jan. 21, 2010 for U.S. Appl. No. 11/122,581.

* cited by examiner

INPUT/OUTPUT FILE FORMATS — 2001
DATA SUPPLIER ENCRYPTION INPUT FILE FORMAT

| LENGTH | START | END | FIELD NAME | DESCRIPTION |
|---|---|---|---|---|
| 7 | 1 | 7 | PHARMACY NCPDP NUMBER (FORMALLY NABP NUMBER) | UNIQUE STORE NUMBER (HARD-CODED IN PROGRAM) ID ASSIGNED TO PHARMACY. NCPDP FORMAT=SSNNNNC, SS=STATE CODE, NNNN=NUMBER, C=CHECK DIGIT |
| 7 | 8 | 14 | SUPPLIER DEFINED STORE NUMBER | CUSTOM STORE NUMBER USED BY SUPPLIER TO IDENTIFY OUTLETS |
| 4 | 15 | 18 | MAIL SERVICE NUMBER | NUMBER SUPPLIED BY IMS FOR MAIL SERVICE SUPPLIERS ONLY |
| 9 | 19 | 27 | PHARMACY ZIP CODE | ZIP CODE OF PHARMACY |
| 15 | 28 | 42 | PRESCRIPTION NUMBER | PRESCRIPTION NUMBER ASSIGNED BY THE PHARMACY |
| 8 | 43 | 50 | DATE WRITTEN | DATE PRESCRIPTION WAS WRITTEN BY THE PRESCRIBER (CCYYMMDD) |
| 8 | 51 | 58 | DATE FILLED | DATE PRESCRIPTION FILLED BY PHARMACIST (CCYYMMDD) |
| 8 | 59 | 66 | DATE DELIVERED/ FULFILLED | DATE PRESCRIPTION WAS DELIVERED TO PATIENT. DATE OF TRANSACTION. (CCYYMMDD) |
| 2 | 67 | 68 | NEW/REFILL CODE | 00 = NEW, 1 - 99 = NUMBER OF REFILLS |
| 11 | 69 | 79 | DISPENSED NDC NUMBER | NDC IDENTIFYING THE DRUG DISPENSED |
| 28 | 80 | 107 | DISPENSED DRUG NAME | NAME OF THE DRUG DISPENSED, INCLUDING FORM AND STRENGTH |
| 11 | 108 | 118 | PRESCRIBED NDC NUMBER | NDC IDENTIFYING THE DRUG PRESCRIBED |
| 28 | 119 | 146 | PRESCRIBED DRUG NAME | NAME OF THE DRUG PRESCRIBED, INCLUDING FORM AND STRENGTH |
| 1 | 147 | 147 | PARTIAL FILL STATUS | CODE INDICATING THE STATUS OF A TRANSACTION AS A PARTIAL FILL. P=PARTIAL FILL, C=COMPLETION OF PARTIAL FILL, BLANK=NOT SPECIFIED |
| 7.3 | 148 | 157 | METRIC QUANTITY | NUMBER OF METRIC UNITS OF MEDICATION DISPENSED. DECIMAL PLACEMENT IS NECESSARY TO USE WHEN DISPENSING QUANTITIES LESS THAN 1. 2 POSITION IMPLIED DECIMAL (99999V99) |
| 3 | 158 | 160 | DAYS SUPPLY | NUMBER OF DAYS THE PRESCRIPTION WILL LAST |
| 6.2 | 161 | 168 | INGREDIENT COST | COST (TO THE PHARMACY) OF THE DRUG DISPENSED.. 2 POSITION IMPLIED DECIMAL (99999V99) |

FIG. 2A

| LENGTH | START | END | FIELD NAME | DESCRIPTION |
|---|---|---|---|---|
| 6.2 | 169 | 176 | INGREDIENT COST PAID | INGREDIENT COST PAID TO THE PHARMACY BY THE THIRD PARTY IN A THIRD PARTY TRANSACTION (99999V99) |
| 6.2 | 177 | 184 | DISPENSING FEE | DISPENSING FEE SUBMITTED TO THIRD PARTY PROCESSOR 2 POSITION IMPLIED DECIMAL (99999V99) |
| 6.2 | 185 | 192 | DISPENSING FEE PAID | DISPENSING FEE PAID BY THIRD PARTY PROCESSOR (99999V99) |
| 6.2 | 193 | 200 | CO-PAY /COINSURANCE AMOUNT | COPAY/COINSURANCE AMOUNT PAID BY PATIENT ON A THIRD PARTY TRANSACTION 2 POSITION IMPLIED DECIMAL (99999V99) |
| 6.2 | 201 | 208 | TOTAL AMOUNT PAID BY PATIENT | TOTAL AMOUNT OWED TO PHARMACY BY PATIENT AT POINT OF TRANSACTION (99999V99) |
| 6.2 | 209 | 216 | REIMBURSED AMOUNT | TOTAL AMOUNT REIMBURSED BY THIRD PARTY PAYER 2 POSITION IMPLIED DECIMAL (99999V99) |
| 1 | 217 | 217 | BASIS OF INGREDIENT COST SUBMITTED | CODE INDICATING THE METHOD BY WHICH 'INGREDIENT COST SUBMITTED' WAS CALCULATED M=MAC A=AWP U=USUAL AND CUSTOMARY O=OTHER |
| 1 | 218 | 218 | BASIS OF INGREDIENT COST REIMBURSED | CODE INDICATING THE METHOD BY WHICH THE REIMBURSEMENT WAS CALCULATED FOR 'INGREDIENT COST PAID' M=MAC A=AWP U=USUAL AND CUSTOMARY O=OTHER |
| 6.2 | 219 | 226 | GROSS AMOUNT DUE | THE TOTAL PRESCRIPTION PRICE CLAIMED OR EXPECTED REIMBURSEMENT FROM ALL SOURCES (TOTAL PATIENT PAY + THIRD PARTY REIMBURSEMENT). 2 POSITION IMPLIED DECIMAL (99999V99) |
| 1 | 227 | 227 | PAYMENT TYPE | 1=CASH, 2=MEDICAID, 3=THIRD PARTY |
| 2 | 228 | 229 | INDICATOR FOR COUPON TYPE | 1-PRICE DISCOUNT 2-FREE PRODUCT 99-OTHER |
| 6.2 | 230 | 237 | COUPON FACE VALUE | 2 POSITION IMPLIED DECIMAL (99999V99) |
| 15 | 238 | 252 | COUPON ID # | SKU OR OTHER NUMBER IDENTIFYING COUPON |
| 2 | 253 | 254 | INDICATOR FOR VOUCHERS, FREE GOODS, DISCOUNTS, OR INDIGENT PROGRAMS | 1-VOUCHER 2-FREE GOODS 3-DISCOUNTED GOODS 4-INDIGENT PROGRAM |
| 9 | 255 | 263 | PLAN CODE | PLAN CODE WHICH MAPS TO RETAILER SPECIFIC PLAN DICTIONARY PROVIDE TO IMS |
| 2 | 264 | 265 | INDICATOR FOR DISCOUNT CASH CARD PROGRAM | Y-PATIENT USED DISCOUNT CASH CARD PLAN |

FIG. 2A (Cont.)

| LENGTH | START | END | FIELD NAME | DESCRIPTION |
|---|---|---|---|---|
| 15 | 266 | 280 | GROUP NUMBER | ID ASSIGNED TO CARDHOLDER GROUP OR EMPLOYER GROUP |
| 6 | 281 | 286 | BANK IDENTIFICATION NUMBER (BIN) | STANDARD NUMBER USED FOR NETWORK ROUTING |
| 2 | 287 | 288 | NUMBER OF REFILLS AUTHORIZED | NUMBER OF REFILLS AUTHORIZED BY PRESCRIBER |
| 2 | 289 | 290 | REFILLS REMAINING | NUMBER OF REFILLS REMAINING ON RX |
| 1 | 291 | 291 | DISPENSED AS WRITTEN | NCPDP CODE (BELOW) INDICATING WHETHER THE PRESCRIBER'S INSTRUCTIONS WERE FOLLOWED |
| 15 | 292 | 306 | PRESCRIBER LAST NAME | PRESCRIBING PHYSICIAN'S LAST NAME |
| 10 | 307 | 316 | PRESCRIBER FIRST NAME | PRESCRIBING PHYSICIAN'S FIRST NAME |
| 1 | 317 | 317 | PRESCRIBER MIDDLE INITIAL | PRESCRIBING PHYSICIAN'S MIDDLE INITIAL |
| 9 | 318 | 326 | PRESCRIBER DEA NUMBER | PRESCRIBING PHYSICIAN'S DEA NUMBER |
| 15 | 327 | 341 | STATE LICENSE NUMBER FOR PRESCRIBER | PRESCRIBER'S STATE LICENSE NUMBER |
| 2 | 342 | 343 | STATE OF ASSIGNED NUMBER FOR PRESCRIBER | STATE WHICH ASSIGNED ABOVE NUMBER |
| 10 | 344 | 353 | INDUSTRY STANDARD NUMBER FOR PRESCRIBERS (WHEN IT BECOMES AVAILABLE) | INDUSTRY STANDARD NUMBER ASSIGNED TO THE PRESCRIBER FOR FUTURE USE PENDING IMPLEMENTATION OF NPI OR OTHER HCFA MANDATED NATIONAL STANDARD |
| 15 | 354 | 368 | PRESCRIBER CITY | PRESCRIBING PHYSICIAN'S CITY |
| 2 | 369 | 370 | PRESCRIBER STATE | PRESCRIBING PHYSICIAN'S STATE |
| 5 | 371 | 375 | PRESCRIBER ZIP CODE | PRESCRIBING PHYSICIAN'S ZIP CODE |
| 10 | 376 | 385 | PRESCRIBER PHONE NUMBER | PRESCRIBER'S OFFICE PHONE CONTACT NUMBER |
| 10 | 386 | 395 | PRESCRIBER FAX NUMBER | PRESCRIBER'S OFFICE FAX CONTACT NUMBER |
| 4 | 396 | 399 | PATIENT BIRTH YEAR | BIRTH YEAR OF PATIENT CCYY IF PATIENT IS 89 OR OLDER = 0000 |
| 2 | 400 | 401 | FILLER | |
| 1 | 402 | 402 | PATIENT GENDER CODE | SEX OF PATIENT (1=MALE, 2=FEMALE, 3=UNSPECIFIED) |

FIG. 2A (Cont.)

| LENGTH | START | END | FIELD NAME | DESCRIPTION |
|---|---|---|---|---|
| 5 | 403 | 407 | PATIENT ZIP CODE (HIPAA) | PATIENT'S ZIP CODE 3 DIGIT AND 2 ZEROS POPULATIONS OF 20,000 AND BELOW=ALL ZEROS |
| 2 | 408 | 409 | PATIENT LOCATION CODE | CODE IDENTIFYING THE LOCATION OF THE PATIENT WHEN RECEIVING SERVICES FROM THE PHARMACY. 0-NOT SPECIFIED, 1-HOME, 2-INTER-CARE, 3-NURSING HOME, 4-LTC/EXTENDED CARE, 5-REST HOME, 6-BOARDING HOME, 7-SKILLED CARE FACILITY, 8-SUB-ACUTE FACILITY, 9-ACUTE CARE FACILITY, 10-OUTPATIENT, 11-HOSPICE, 12-PRISON (PENDING NCPDP DEFINITIONS) |
| 11 | 410 | 420 | DE-IDENTIFIED PATIENT CODE | CONSISTENT, TRACKABLE, UNIQUE IDENTIFIER WHICH MASKS IDENTIFICATION OF ANY PATIENT. |
| 1 | 421 | 421 | ORIGIN OF RX | 1=WRITTEN 2=TELEPHONE 3=ELECTRONIC 4=FACSIMILE |
| 1 | 422 | 422 | INDICATOR FOR E-PRESCRIBED TRANSACTION | Y=PRESCRIPTION WRITTEN VIA EPRESCRIBING NETWORK; BLANK OTHERWISE |
| 1 | 423 | 423 | LEVEL OF SERVICE (WAS DISPENSED INDICATOR) | 1=PATIENT CONSULTATION 2=HOME DELIVERY 3=EMERGENCY 4=24 HOUR SERVICE 5=PATIENT CONSULTATION REGARDING GENERIC PRODUCT SELECTION 6=IN HOME SERVICE |
| 1 | 424 | 424 | CENTRAL FILL FLAG (IF APPLICABLE) | Y=YES N=NO INDICATES WHETHER SCRIPT WAS FILLED AT A CENTRAL FILL LOCATION. INDICATE "N" IF ADJUDICATED AT A CENTRAL LOCATION BUT NOT FILLED AT A CENTRAL LOCATION. |
| 1 | 425 | 425 | CLAIM INDICATOR | D=DISPENSED, R=REVERSAL |
| 10 | 426 | 435 | PROCESSOR CONTROL NUMBER (PCN) | NUMBER ASSIGNED BY PROCESSOR REQUIRED FOR CLAIMS PROCESSING |
| 1 | 436 | 436 | COMPOUND CODE | CODE INDICATING WHETHER OR NOT THE PRESCRIPTION IS A COMPOUND (0=NOT SPECIFIED, 1=NOT A COMPOUND, 2=COMPOUND) |
| 2 | 437 | 438 | CHAIN CODE | SUPPLIER ASSIGNED INDICATOR TO IDENTIFY CHAIN COMPANY |
| 10 | 439 | 448 | DIAGNOSIS CODE | DIAGNOSIS CODE ICD9 OR ICD10 CODE IF AVAILABLE |
| 8 | 449 | 456 | DRUG STRENGTH QUANTITY (IF AVAILABLE) | ACTUAL STRENGTH DISPENSED FOR INJECTABLES. |
| 14 | 457 | 470 | FILLER | FOR FUTURE USE |
| 10 | 501 | 510 | PATIENT DATE OF BIRTH | PATIENT FULL DATE OF BIRTH. EXPECTS NCPDP FORMAT HOWEVER APPLICATION WILL CONVERT COMMON DATE FORMAT AS OUTLINED BY THE PATIENT DATE OF BIRTH FORMAT INDICATOR |

FIG. 2A (Cont.)

| LENGTH | START | END | FIELD NAME | DESCRIPTION |
|---|---|---|---|---|
| 20 | 511 | 530 | CARDHOLDER ID | INSURANCE ID ASSIGNED TO THE CARDHOLDER |
| 20 | 531 | 550 | RECORD NUMBER | UNIQUE IDENTIFIER ASSIGNED BY THE DATA SUPPLIER TO IDENTIFY THE HEALTHCARE TRANSACTION<br>FOR PHARMACY DATA, THE PRESCRIPTION NUMBER ASSIGNED TO THE TRANSACTION |
| 5 | 551 | 555 | PATIENT ZIP | FIVE DIGIT ZIP CODE FOR THE PATIENT INVOLVED WITH THE HEALTHCARE TRANSACTION<br>ASSUMES DATA SUPPLIER HAS VALIDATED THE ZIP CODE AS VALID |
| 12 | 556 | 567 | PATIENT FIRST NAME | FIRST NAME OF THE PATIENT INVOLVED IN THE TRANSACTION<br>SUPPLIED BY DATA SUPPLIER'S PROCESSING ENVIRONMENT |
| 15 | 568 | 582 | PATIENT LAST NAME | LAST NAME OF THE PATIENT INVOLVED IN THE TRANSACTION<br>SUPPLIED BY DATA SUPPLIER'S PROCESSING ENVIRONMENT |
| 30 | 583 | 612 | PATIENT STREET ADDRESS | PATIENT'S ADDRESS LINE CONTAINING THE STREET NUMBER OF THE ADDRESS<br>SUPPLIED BY DATA SUPPLIER'S PROCESSING ENVIRONMENT |
| 20 | 613 | 632 | NCPDP PATIENT ID | DATA SUPPLIER'S ASSIGNED IDENTIFIER TO IDENTIFY A PATIENT<br>SUPPLIED BY DATA SUPPLIER'S PROCESSING ENVIRONMENT. |
| 2 | 633 | 634 | PATIENT ID QUALIFIER | CODE QUALIFYING THE PATIENT ID (ABOVE)<br>ANY OTHER QUALIFIER FORMATTING VARIATIONS WILL NEED TO BE TRANSFORMED INTO AN ACCEPTED FORM BY THE CALLING APPLICATION<br>01 - SSN<br>02 - DRIVER'S LICENSE NUMBER<br>03 - US MILITARY ID<br>04 - DATA SUPPLIER ID<br>05 - FUTURE USE<br>06 - FUTURE USE<br>99 - OTHER<br>BLANK - NOT SPECIFIED |

FIG. 2A (Cont.)

DATA SUPPLIER ENCRYPTION OUTPUT FILE FORMAT — 2002

| LENGTH | START | END | FIELD NAME | DESCRIPTION |
|---|---|---|---|---|
| 7 | 1 | 7 | PHARMACY NCPDP NUMBER (FORMALLY NABP NUMBER) | UNIQUE STORE NUMBER (HARD-CODED IN PROGRAM) ID ASSIGNED TO PHARMACY. NCPDP FORMAT=SSNNNNC, SS=STATE CODE, NNNN=NUMBER, C=CHECK DIGIT |
| 7 | 8 | 14 | SUPPLIER DEFINED STORE NUMBER | CUSTOM STORE NUMBER USED BY SUPPLIER TO IDENTIFY OUTLETS |
| 4 | 15 | 18 | MAIL SERVICE NUMBER | NUMBER SUPPLIED BY IMS FOR MAIL SERVICE SUPPLIERS ONLY |
| 9 | 19 | 27 | PHARMACY ZIP CODE | ZIP CODE OF PHARMACY |
| 15 | 28 | 42 | PRESCRIPTION NUMBER | PRESCRIPTION NUMBER ASSIGNED BY THE PHARMACY |
| 8 | 43 | 50 | DATE WRITTEN | DATE PRESCRIPTION WAS WRITTEN BY THE PRESCRIBER (CCYYMMDD) |
| 8 | 51 | 58 | DATE FILLED | DATE PRESCRIPTION FILLED BY PHARMACIST (CCYYMMDD) |
| 8 | 59 | 66 | DATE DELIVERED/ FULFILLED | DATE PRESCRIPTION WAS DELIVERED TO PATIENT. DATE OF TRANSACTION. (CCYYMMDD) |
| 2 | 67 | 68 | NEW/REFILL CODE | 00 = NEW, 1 - 99 = NUMBER OF REFILLS |
| 11 | 69 | 79 | DISPENSED NDC NUMBER | NDC IDENTIFYING THE DRUG DISPENSED |
| 28 | 80 | 107 | DISPENSED DRUG NAME | NAME OF THE DRUG DISPENSED, INCLUDING FORM AND STRENGTH |
| 11 | 108 | 118 | PRESCRIBED NDC NUMBER | NDC IDENTIFYING THE DRUG PRESCRIBED |
| 28 | 119 | 146 | PRESCRIBED DRUG NAME | NAME OF THE DRUG PRESCRIBED, INCLUDING FORM AND STRENGTH |
| 1 | 147 | 147 | PARTIAL FILL STATUS | CODE INDICATING THE STATUS OF A TRANSACTION AS A PARTIAL FILL. P=PARTIAL FILL, C=COMPLETION OF PARTIAL FILL, BLANK=NOT SPECIFIED |
| 7.3 | 148 | 157 | METRIC QUANTITY | NUMBER OF METRIC UNITS OF MEDICATION DISPENSED. DECIMAL PLACEMENT IS NECESSARY TO USE WHEN DISPENSING QUANTITIES LESS THAN 1. 2 POSITION IMPLIED DECIMAL (99999V99) |
| 3 | 158 | 160 | DAYS SUPPLY | NUMBER OF DAYS THE PRESCRIPTION WILL LAST |
| 6.2 | 161 | 168 | INGREDIENT COST | COST (TO THE PHARMACY) OF THE DRUG DISPENSED. . 2 POSITION IMPLIED DECIMAL (99999V99) |
| 6.2 | 169 | 176 | INGREDIENT COST PAID | INGREDIENT COST PAID TO THE PHARMACY BY THE THIRD PARTY IN A THIRD PARTY TRANSACTION (99999V99) |
| 6.2 | 177 | 184 | DISPENSING FEE | DISPENSING FEE SUBMITTED TO THIRD PARTY PROCESSOR 2 POSITION IMPLIED DECIMAL (99999V99) |

FIG. 2B

| LENGTH | START | END | FIELD NAME | DESCRIPTION |
|---|---|---|---|---|
| 6.2 | 185 | 192 | DISPENSING FEE PAID | DISPENSING FEE PAID BY THIRD PARTY PROCESSOR (99999V99) |
| 6.2 | 193 | 200 | CO-PAY /COINSURANCE AMOUNT | COPAY/COINSURANCE AMOUNT PAID BY PATIENT ON A THIRD PARTY TRANSACTION 2 POSITION IMPLIED DECIMAL (9999V99) |
| 6.2 | 201 | 208 | TOTAL AMOUNT PAID BY PATIENT | TOTAL AMOUNT OWED TO PHARMACY BY PATIENT AT POINT OF TRANSACTION (99999V99) |
| 6.2 | 209 | 216 | REIMBURSED AMOUNT | TOTAL AMOUNT REIMBURSED BY THIRD PARTY PAYER 2 POSITION IMPLIED DECIMAL (99999V99) |
| 1 | 217 | 217 | BASIS OF INGREDIENT COST SUBMITTED | CODE INDICATING THE METHOD BY WHICH 'INGREDIENT COST SUBMITTED' WAS CALCULATED M=MAC A=AWP U=USUAL AND CUSTOMARY O=OTHER |
| 1 | 218 | 218 | BASIS OF INGREDIENT COST REIMBURSED | CODE INDICATING THE METHOD BY WHICH THE REIMBURSEMENT WAS CALCULATED FOR 'INGREDIENT COST PAID' M=MAC A=AWP U=USUAL AND CUSTOMARY O=OTHER |
| 6.2 | 219 | 226 | GROSS AMOUNT DUE | THE TOTAL PRESCRIPTION PRICE CLAIMED OR EXPECTED REIMBURSEMENT FROM ALL SOURCES (TOTAL PATIENT PAY + THIRD PARTY REIMBURSEMENT). 2 POSITION IMPLIED DECIMAL (99999V99) |
| 1 | 227 | 227 | PAYMENT TYPE | 1=CASH, 2=MEDICAID, 3=THIRD PARTY |
| 2 | 228 | 229 | INDICATOR FOR COUPON TYPE | :1-PRICE DISCOUNT 2-FREE PRODUCT 99-OTHER |
| 6.2 | 230 | 237 | COUPON FACE VALUE | 2 POSITION IMPLIED DECIMAL (99999V99) |
| 15 | 238 | 252 | COUPON ID # | SKU OR OTHER NUMBER IDENTIFYING COUPON |
| 2 | 253 | 254 | INDICATOR FOR VOUCHERS, FREE GOODS, DISCOUNTS, OR INDIGENT PROGRAMS | 1-VOUCHER 2-FREE GOODS 3-DISCOUNTED GOODS 4-INDIGENT PROGRAM |
| 9 | 255 | 263 | PLAN CODE | PLAN CODE WHICH MAPS TO RETAILER SPECIFIC PLAN DICTIONARY PROVIDE TO IMS |
| 2 | 264 | 265 | INDICATOR FOR DISCOUNT CASH CARD PROGRAM | Y-PATIENT USED DISCOUNT CASH CARD PLAN |
| 15 | 266 | 280 | GROUP NUMBER | ID ASSIGNED TO CARDHOLDER GROUP OR EMPLOYER GROUP |
| 6 | 281 | 286 | BANK IDENTIFICATION NUMBER (BIN) | STANDARD NUMBER USED FOR NETWORK ROUTING |

FIG. 2B (Cont.)

| LENGTH | START | END | FIELD NAME | DESCRIPTION |
|---|---|---|---|---|
| 2 | 287 | 288 | NUMBER OF REFILLS AUTHORIZED | NUMBER OF REFILLS AUTHORIZED BY PRESCRIBER |
| 2 | 289 | 290 | REFILLS REMAINING | NUMBER OF REFILLS REMAINING ON RX |
| 1 | 291 | 291 | DISPENSED AS WRITTEN | NCPDP CODE (BELOW) INDICATING WHETHER THE PRESCRIBER'S INSTRUCTIONS WERE FOLLOWED |
| 15 | 292 | 306 | PRESCRIBER LAST NAME | PRESCRIBING PHYSICIAN'S LAST NAME |
| 10 | 307 | 316 | PRESCRIBER FIRST NAME | PRESCRIBING PHYSICIAN'S FIRST NAME |
| 1 | 317 | 317 | PRESCRIBER MIDDLE INITIAL | PRESCRIBING PHYSICIAN'S MIDDLE INITIAL |
| 9 | 318 | 326 | PRESCRIBER DEA NUMBER | PRESCRIBING PHYSICIAN'S DEA NUMBER |
| 15 | 327 | 341 | STATE LICENSE NUMBER FOR PRESCRIBER | PRESCRIBER'S STATE LICENSE NUMBER |
| 2 | 342 | 343 | STATE OF ASSIGNED NUMBER FOR PRESCRIBER | STATE WHICH ASSIGNED ABOVE NUMBER |
| 10 | 344 | 353 | INDUSTRY STANDARD NUMBER FOR PRESCRIBERS (WHEN IT BECOMES AVAILABLE) | INDUSTRY STANDARD NUMBER ASSIGNED TO THE PRESCRIBER FOR FUTURE USE PENDING IMPLEMENTATION OF NPI OR OTHER HCFA MANDATED NATIONAL STANDARD |
| 15 | 354 | 368 | PRESCRIBER CITY | PRESCRIBING PHYSICIAN'S CITY |
| 2 | 369 | 370 | PRESCRIBER STATE | PRESCRIBING PHYSICIAN'S STATE |
| 5 | 371 | 375 | PRESCRIBER ZIP CODE | PRESCRIBING PHYSICIAN'S ZIP CODE |
| 10 | 376 | 385 | PRESCRIBER PHONE NUMBER | PRESCRIBER'S OFFICE PHONE CONTACT NUMBER |
| 10 | 386 | 395 | PRESCRIBER FAX NUMBER | PRESCRIBER'S OFFICE FAX CONTACT NUMBER |
| 4 | 396 | 399 | PATIENT BIRTH YEAR | BIRTH YEAR OF PATIENT CCYY IF PATIENT IS 89 OR OLDER = 0000 |
| 2 | 400 | 401 | FILLER | |
| 1 | 402 | 402 | PATIENT GENDER CODE | SEX OF PATIENT (1=MALE, 2=FEMALE, 3=UNSPECIFIED) |
| 5 | 403 | 407 | PATIENT ZIP CODE | PATIENT'S ZIP CODE 3 DIGIT AND 2 ZEROS POPULATIONS OF 20,000 AND BELOW=ALL ZEROS |

FIG. 2B (Cont.)

| LENGTH | START | END | FIELD NAME | DESCRIPTION |
|---|---|---|---|---|
| 2 | 408 | 409 | PATIENT LOCATION CODE | CODE IDENTIFYING THE LOCATION OF THE PATIENT WHEN RECEIVING SERVICES FROM THE PHARMACY. 0-NOT SPECIFIED, 1-HOME, 2-INTER-CARE, 3-NURSING HOME, 4-LTC/EXTENDED CARE, 5-REST HOME, 6-BOARDING HOME, 7-SKILLED CARE FACILITY, 8-SUB-ACUTE FACILITY, 9-ACUTE CARE FACILITY, 10-OUTPATIENT, 11-HOSPICE, 12-PRISON (PENDING NCPDP DEFINITIONS) |
| 11 | 410 | 420 | DE-IDENTIFIED PATIENT CODE | CONSISTENT, TRACKABLE, UNIQUE IDENTIFIER THAT MASKS IDENTIFICATION OF ANY PATIENT. |
| 1 | 421 | 421 | ORIGIN OF RX | 1=WRITTEN 2=TELEPHONE 3=ELECTRONIC 4=FACSIMILE |
| 1 | 422 | 422 | INDICATOR FOR E-PRESCRIBED TRANSACTION | Y=PRESCRIPTION WRITTEN VIA EPRESCRIBING NETWORK; BLANK OTHERWISE |
| 1 | 423 | 423 | LEVEL OF SERVICE (WAS DISPENSED INDICATOR) | 1=PATIENT CONSULTATION 2=HOME DELIVERY 3=EMERGENCY 4=24 HOUR SERVICE 5=PATIENT CONSULTATION REGARDING GENERIC PRODUCT SELECTION 6=IN HOME SERVICE |
| 1 | 424 | 424 | CENTRAL FILL FLAG (IF APPLICABLE) | Y=YES N=NO INDICATES WHETHER SCRIPT WAS FILLED AT A CENTRAL FILL LOCATION. INDICATE "N" IF ADJUDICATED AT A CENTRAL LOCATION BUT NOT FILLED AT A CENTRAL LOCATION. |
| 1 | 425 | 425 | CLAIM INDICATOR | D=DISPENSED, R=REVERSAL |
| 10 | 426 | 435 | PROCESSOR CONTROL NUMBER (PCN) | NUMBER ASSIGNED BY PROCESSOR REQUIRED FOR CLAIMS PROCESSING |
| 1 | 436 | 436 | COMPOUND CODE | CODE INDICATING WHETHER OR NOT THE PRESCRIPTION IS A COMPOUND (0=NOT SPECIFIED, 1=NOT A COMPOUND, 2=COMPOUND) |
| 2 | 437 | 438 | CHAIN CODE | SUPPLIER ASSIGNED INDICATOR TO IDENTIFY CHAIN COMPANY |
| 10 | 439 | 448 | DIAGNOSIS CODE | DIAGNOSIS CODE ICD9 OR ICD10 CODE IF AVAILABLE |
| 8 | 449 | 456 | DRUG STRENGTH QUANTITY (IF AVAILABLE) | ACTUAL STRENGTH DISPENSED FOR INJECTABLES. |
| 14 | 457 | 470 | FILLER | FOR FUTURE USE |
| 3 | 471 | 473 | DATA SUPPLIER ID | UNIQUE IDENTIFIER ASSIGNED TO EACH DATA SUPPLIER USING THE DATA ENCRYPTION APPLICATION. USED FOR FUTURE POTENTIAL DEBUGGING OR ENHANCED ENCRYPTION PROCESSES |
| 8 | 474 | 481 | PROCESSING DATE | DATE IN WHICH THE DATA ENCRYPTION ALGORITHM WAS CALLED. USED IN THE OVERALL PROCESS AUDIT TO CONFIRM THAT IMS' ENCRYPTION PROCESS AND THE DATA SUPPLIER'S ENCRYPTION PROCESS ARE IN-SYNC. CCYYMMDD |

FIG. 2B (Cont.)

| LENGTH | START | END | FIELD NAME | DESCRIPTION |
|---|---|---|---|---|
| 44 | 512 | 555 | PATIENT DATE OF BIRTH | ENCRYPTED PATIENT DATE OF BIRTH |
| 64 | 556 | 619 | CARDHOLDER ID | ENCRYPTED CARDHOLDER ID |
| 64 | 620 | 683 | RECORD NUMBER | ENCRYPTED RECORD NUMBER (IF REQUESTED), ELSE UNENCRYPTED RECORD NUMBER |
| 44 | 684 | 727 | PATIENT ZIP | ENCRYPTED FIVE DIGIT PATIENT ZIP CODE |
| 44 | 728 | 771 | PATIENT FIRST NAME | ENCRYPTED PATIENT FIRST NAME |
| 44 | 772 | 815 | PATIENT LAST NAME | ENCRYPTED PATIENT LAST NAME |
| 44 | 816 | 859 | PATIENT STREET ADDRESS | ENCRYPTED STREET NUMBER FOR THE PATIENT'S STREET ADDRESS |
| 64 | 860 | 923 | NCPDP PATIENT ID | ENCRYPTED NCPDP PATIENT ID |
| 2 | 924 | 925 | PATIENT ID QUALIFIER | CODE QUALIFYING THE PATIENT ID (ABOVE)<br>ANY OTHER QUALIFIER FORMATTING VARIATIONS WILL NEED TO BE TRANSFORMED INTO AN ACCEPTED FORM BY THE CALLING APPLICATION<br>    01 - SSN<br>    02 - DRIVER'S LICENSE NUMBER<br>    03 - US MILITARY ID<br>    04 - DATA SUPPLIER ID<br>    05 - FUTURE USE<br>    06 - FUTURE USE<br>    99 - OTHER.<br>BLANK - NOT SPECIFIED |
| 5 | 926 | 930 | HIPAA PATIENT ZIP | HIPAA COMPLIANT PATIENT DATE OF BIRTH AS PER THE HIPAA PRIVACY COMPLIANCE USE CASE. |
| 8 | 931 | 938 | HIPAA PATIENT DATE OF BIRTH | HIPAA COMPLIANT PATIENT DATE OF BIRTH AS PER THE HIPAA PRIVACY COMPLIANCE USE CASE. |

FIG. 2B (Cont.)

IMS ENCRYPTION INPUT FILE FORMAT ⟵ 2003

| LENGTH | START | END | FIELD NAME | DESCRIPTION |
|---|---|---|---|---|
| 1 | 1 | 1 | PATIENT GENDER CODE | SEX OF PATIENT (1=MALE, 2=FEMALE, 3=UNSPECIFIED) |
| 3 | 2 | 5 | DATA SUPPLIER ID | UNIQUE IDENTIFIER ASSIGNED TO EACH DATA SUPPLIER USING THE DATA ENCRYPTION APPLICATION. USED FOR FUTURE POTENTIAL DEBUGGING OR ENHANCED ENCRYPTION PROCESSES |
| 8 | 6 | 13 | PROCESSING DATE | DATE IN WHICH THE DATA ENCRYPTION ALGORITHM WAS CALLED. USED IN THE OVERALL PROCESS AUDIT TO CONFIRM THAT IMS' ENCRYPTION PROCESS AND THE DATA SUPPLIER'S ENCRYPTION PROCESS ARE IN-SYNC. CCYYMMDD |
| 50 | 14 | 43 | MATCHING ATTRIBUTE | ATTRIBUTE USED TO STORE THE INFORMATION NEEDED TO MATCH THE ENCRYPTED ATTRIBUTE CONTENTS BACK TO A DATA SUPPLIER'S UNIQUE TRANSACTION. DATA SUPPLIER / IMPLEMENTATION PARTNER CAN POPULATE THIS FIELD WITH ANY VALUE(S) IT WILL NEED IN SUBSEQUENT PROCESS TO LINK THE ENCRYPTED DATA BACK TO A SPECIFIC TRANSACTION |
| 44 | 44 | 87 | PATIENT DATE OF BIRTH | DATA SUPPLIER ENCRYPTED PATIENT DATE OF BIRTH |
| 64 | 88 | 151 | CARDHOLDER ID | DATA SUPPLIER ENCRYPTED CARDHOLDER ID |
| 64 | 152 | 215 | RECORD NUMBER | DATA SUPPLIER ENCRYPTED RECORD NUMBER (IF PROVIDED) |
| 44 | 216 | 259 | PATIENT ZIP | DATA SUPPLIER ENCRYPTED PATIENT ZIP |
| 44 | 260 | 303 | PATIENT FIRST NAME | DATA SUPPLIER ENCRYPTED PATIENT FIRST NAME |
| 44 | 304 | 347 | PATIENT LAST NAME | DATA SUPPLIER ENCRYPTED PATIENT LAST NAME |
| 44 | 348 | 391 | PATIENT STREET ADDRESS | DATA SUPPLIER ENCRYPTED STREET NUMBER (REMOVED FROM THE COMPLETE STREET ADDRESS) |
| 64 | 392 | 455 | NCPDP PATIENT ID | DATA SUPPLIER ENCRYPTED NCPDP PATIENT ID |
| 2 | 456 | 457 | PATIENT ID QUALIFIER | CODE QUALIFYING THE PATIENT ID (ABOVE) ANY OTHER QUALIFIER FORMATTING VARIATIONS WILL NEED TO BE TRANSFORMED INTO AN ACCEPTED FORM BY THE CALLING APPLICATION<br>01 - SSN<br>02 - DRIVER'S LICENSE NUMBER<br>03 - US MILITARY ID<br>04 - DATA SUPPLIER ID<br>05 - FUTURE USE<br>06 - FUTURE USE<br>99 - OTHER<br>BLANK - NOT SPECIFIED |

FIG. 2C

IMS ENCRYPTION OUTPUT FILE FORMAT — 2004

| LENGTH | START | END | FIELD NAME | DESCRIPTION |
|---|---|---|---|---|
| 1 | 1 | 1 | PATIENT GENDER CODE | SEX OF PATIENT (1=MALE, 2=FEMALE, 3=UNSPECIFIED) |
| 3 | 2 | 5 | DATA SUPPLIER ID | UNIQUE IDENTIFIER ASSIGNED TO EACH DATA SUPPLIER USING THE DATA ENCRYPTION APPLICATION. USED FOR FUTURE POTENTIAL DEBUGGING OR ENHANCED ENCRYPTION PROCESSES |
| 8 | 6 | 13 | PROCESSING DATE | DATE IN WHICH THE DATA ENCRYPTION ALGORITHM WAS CALLED. USED IN THE OVERALL PROCESS AUDIT TO CONFIRM THAT IMS' ENCRYPTION PROCESS AND THE DATA SUPPLIER'S ENCRYPTION PROCESS ARE IN-SYNC. CCYYMMDD |
| 50 | 14 | 43 | MATCHING ATTRIBUTE | ATTRIBUTE USED TO STORE THE INFORMATION NEEDED TO MATCH THE ENCRYPTED ATTRIBUTE CONTENTS BACK TO A DATA SUPPLIER'S UNIQUE TRANSACTION. DATA SUPPLIER / IMPLEMENTATION PARTNER CAN POPULATE THIS FIELD WITH ANY VALUE(S) IT WILL NEED IN SUBSEQUENT PROCESS TO LINK THE ENCRYPTED DATA BACK TO A SPECIFIC TRANSACTION |
| 44 | 44 | 87 | PATIENT DATE OF BIRTH | IMS ENCRYPTED PATIENT DATE OF BIRTH |
| 64 | 88 | 151 | CARDHOLDER ID | IMS ENCRYPTED CARDHOLDER ID |
| 64 | 152 | 215 | RECORD NUMBER | IMS ENCRYPTED RECORD NUMBER (IF REQUIRED) |
| 44 | 216 | 259 | PATIENT ZIP | IMS ENCRYPTED PATIENT ZIP |
| 44 | 260 | 303 | PATIENT FIRST NAME | IMS ENCRYPTED PATIENT FIRST NAME |
| 44 | 304 | 347 | PATIENT LAST NAME | IMS ENCRYPTED PATIENT LAST NAME |
| 44 | 348 | 391 | PATIENT STREET ADDRESS | IMS ENCRYPTED PATIENT STREET ADDRESS (HOUSE NUMBER ONLY) |
| 64 | 392 | 455 | NCPDP PATIENT ID | IMS ENCRYPTED NCPDP PATIENT ID |
| 2 | 456 | 457 | PATIENT ID QUALIFIER | CODE QUALIFYING THE PATIENT ID (ABOVE) ANY OTHER QUALIFIER FORMATTING VARIATIONS WILL NEED TO BE TRANSFORMED INTO AN ACCEPTED FORM BY THE CALLING APPLICATION<br>01 - SSN<br>02 - DRIVER'S LICENSE NUMBER<br>03 - US MILITARY ID<br>04 - DATA SUPPLIER ID<br>05 - FUTURE USE<br>06 - FUTURE USE<br>99 - OTHER<br>BLANK - NOT SPECIFIED |

FIG. 2D

LONGITUDINAL ENCRYPTION KEY

| NAME | DESCRIPTION | FORMAT | VALID VALUES | COMMENTS |
|------|-------------|--------|--------------|----------|
| DATA SUPPLIER ENCRYPTED LONGITUDINAL KEY | ENCRYPTION KEY PROVIDED BY THE KEY ADMINISTRATOR | X(16) | UNIVERSAL ACROSS ALL PARTICIPATING DATA SUPPLIERS | KEY IS PROVIDED IN AN ENCRYPTED FORMAT WHICH IS DECRYPTED BY THE APPLICATION |

DATA SUPPLIER ENCRYPTION KEY

| NAME | DESCRIPTION | FORMAT | VALID VALUES | COMMENTS |
|------|-------------|--------|--------------|----------|
| DATA SUPPLIER ENCRYPTED KEY | ENCRYPTION KEY PROVIDED BY THE KEY ADMINISTRATOR | X(16) | UNIQUE TO THE INDIVIDUAL DATA SUPPLIER | KEY IS PROVIDED IN AN ENCRYPTED FORMAT WHICH IS DECRYPTED BY THE APPLICATION |

IMS LONGITUDINAL ENCRYPTION KEY

| NAME | DESCRIPTION | FORMAT | VALID VALUES | COMMENTS |
|------|-------------|--------|--------------|----------|
| ENCRYPTED IMS LONGITUDINAL KEY | ENCRYPTION KEY PROVIDED BY THE KEY ADMINISTRATOR UNIQUE TO IMS. | X(16) | UNIQUE KEY THAT IS AVAILABLE ONLY TO IMS ENCRYPTION APPLICATION. | KEY IS PROVIDED IN AN ENCRYPTED FORMAT WHICH IS DECRYPTED BY THE APPLICATION |

FIG. 3

- AUDIT FILE FORMATS
DATA SUPPLIER AUDIT ENCRYPTION COUNTS

| NAME | DESCRIPTION | FORMAT | VALID VALUES | COMMENTS |
|---|---|---|---|---|
| DATE | UNIQUE CALENDAR DATE WHEN THE RECORD WAS WRITTEN TO THE DATABASE / FILE | 9(8) | UNIQUE / VALID CALENDAR DATE | ONE RECORD WILL BE STORED FOR EACH CALENDAR DATE IN WHICH THE DATA ENCRYPTION APPLICATION CONDUCTED PROCESSING |
| RECORD RECEIVED COUNT | PROCESS COUNT | 9(8) | INITIALIZED TO ZERO | 1 IS ADDED TO THE COUNTER EACH TIME A RECORD IS SUCCESSFULLY RECEIVED BY THE DATA ENCRYPTION APPLICATION |
| MISSING PATIENT DATE OF BIRTH COUNT | PROCESS COUNT | 9(8) | INITIALIZED TO ZERO | 1 ADDED TO COUNTER EACH TIME A MISSING PATIENT DATE OF BIRTH IS ENCOUNTERED |
| INVALID PATIENT DATE OF BIRTH YEAR COUNT | PROCESS COUNT | 9(8) | INITIALIZED TO ZERO | 1 ADDED TO COUNTER EACH TIME AN INVALID PATIENT DATE OF BIRTH YEAR IS ENCOUNTERED |
| INVALID PATIENT DATE OF BIRTH MONTH COUNT | PROCESS COUNT | 9(8) | INITIALIZED TO ZERO | 1 ADDED TO COUNTER EACH TIME AN INVALID PATIENT DATE OF BIRTH MONTH IS ENCOUNTERED |
| INVALID PATIENT DATE OF BIRTH DAY COUNT | PROCESS COUNT | 9(8) | INITIALIZED TO ZERO | 1 ADDED TO COUNTER EACH TIME AN INVALID PATIENT DATE OF BIRTH DAY IS ENCOUNTERED |
| MISSING PATIENT GENDER COUNT | PROCESS COUNT | 9(8) | INITIALIZED TO ZERO | 1 ADDED TO COUNTER EACH TIME A MISSING PATIENT GENDER ENCOUNTERED |
| INVALID PATIENT GENDER COUNT | PROCESS COUNT | 9(8) | INITIALIZED TO ZERO | 1 ADDED TO COUNTER EACH TIME AN INVALID PATIENT GENDER IS ENCOUNTERED |

FIG. 4A

| NAME | DESCRIPTION | FORMAT | VALID VALUES | COMMENTS |
|---|---|---|---|---|
| MISSING CARDHOLDER ID COUNT | PROCESS COUNT | 9(8) | INITIALIZED TO ZERO | 1 ADDED TO COUNTER EACH TIME A MISSING CARDHOLDER ID IS ENCOUNTERED |
| INVALID CARDHOLDER ID COUNT | PROCESS COUNT | 9(8) | INITIALIZED TO ZERO | 1 ADDED TO COUNTER EACH TIME AN INVALID CARDHOLDER ID IS ENCOUNTERED |
| MISSING RECORD NUMBER COUNT | PROCESS COUNT | 9(8) | INITIALIZED TO ZERO | 1 ADDED TO COUNTER EACH TIME A MISSING RECORD NUMBER IS ENCOUNTERED |
| INVALID RECORD NUMBER COUNT | PROCESS COUNT | 9(8) | INITIALIZED TO ZERO | 1 ADDED TO COUNTER EACH TIME AN INVALID RECORD NUMBER D IS ENCOUNTERED |
| MISSING PATIENT ZIP CODE COUNT | PROCESS COUNT | 9(8) | INITIALIZED TO ZERO | 1 ADDED TO COUNTER EACH TIME A MISSING PATIENT ZIP CODE IS ENCOUNTERED |
| INVALID PATIENT ZIP CODE COUNT | PROCESS COUNT | 9(8) | INITIALIZED TO ZERO | 1 ADDED TO COUNTER EACH TIME AN INVALID PATIENT ZIP CODE IS ENCOUNTERED |
| MISSING PATIENT FIRST NAME COUNT | PROCESS COUNT | 9(8) | INITIALIZED TO ZERO | 1 ADDED TO COUNTER EACH TIME A MISSING PATIENT FIRST NAME IS ENCOUNTERED |
| INVALID PATIENT FIRST NAME COUNT | PROCESS COUNT | 9(8) | INITIALIZED TO ZERO | 1 ADDED TO COUNTER EACH TIME AN INVALID PATIENT FIRST NAME IS ENCOUNTERED |
| MISSING PATIENT LAST NAME COUNT | PROCESS COUNT | 9(8) | INITIALIZED TO ZERO | 1 ADDED TO COUNTER EACH TIME A MISSING PATIENT FIRST NAME IS ENCOUNTERED |
| INVALID PATIENT LAST NAME COUNT | PROCESS COUNT | 9(8) | INITIALIZED TO ZERO | 1 ADDED TO COUNTER EACH TIME AN INVALID PATIENT LAST NAME IS ENCOUNTERED |
| MISSING STREET ADDRESS COUNT | PROCESS COUNT | 9(8) | INITIALIZED TO ZERO | 1 ADDED TO COUNTER EACH TIME A MISSING PATIENT STREET ADDRESS IS ENCOUNTERED |

FIG. 4A (Cont.)

| NAME | DESCRIPTION | FORMAT | VALID VALUES | COMMENTS |
|---|---|---|---|---|
| INVALID PATIENT STREET ADDRESS COUNT | PROCESS COUNT | 9(8) | INITIALIZED TO ZERO | 1 ADDED TO COUNTER EACH TIME AN STREET ADDRESS IS ENCOUNTERED |
| MISSING NCPDP PATIENT ID COUNT | PROCESS COUNT | 9(8) | INITIALIZED TO ZERO | 1 ADDED TO COUNTER EACH TIME A MISSING NCPDP PATIENT ID IS ENCOUNTERED |
| INVALID NCPDP PATIENT ID COUNT | PROCESS COUNT | 9(8) | INITIALIZED TO ZERO | 1 ADDED TO COUNTER EACH TIME AN INVALID NCPDP PATIENT ID IS ENCOUNTERED |
| MISSING PATIENT ID QUALIFIER COUNT | PROCESS COUNT | 9(8) | INITIALIZED TO ZERO | 1 ADDED TO COUNTER EACH TIME A MISSING PATIENT ID QUALIFIER IS ENCOUNTERED |
| INVALID PATIENT ID QUALIFIER COUNT | PROCESS COUNT | 9(8) | INITIALIZED TO ZERO | 1 ADDED TO COUNTER EACH TIME AN INVALID PATIENT ID QUALIFIER IS ENCOUNTERED |
| HIPAA PATIENT YEAR OVER 88 COUNT | PROCESS COUNT | 9(8) | INITIALIZED TO ZERO | 1 ADDED TO COUNTER EACH TIME PATIENT YEAR IS DETERMINED TO BE OVER 88 IN THE HIPAA PRIVACY COMPLIANCE SECTION |
| HIPAA PATIENT ZIP UNDER 20K COUNT | PROCESS COUNT | 9(8) | INITIALIZED TO ZERO | 1 ADDED TO COUNTER EACH TIME PATIENT 3-DIGIT ZIP IS DETERMINED TO BE IN A LOCATION WITH UNDER 20,000 POPULATION IN THE HIPAA PRIVACY COMPLIANCE SECTION |
| DATA OUTPUT RECORD COUNT | PROCESS COUNT | 9(8) | INITIALIZED TO ZERO | 1 ADDED TO COUNTER EACH TIME A RECORD HAS BEEN ENCRYPTED AND RETURNED TO THE CALLING APPLICATION |

FIG. 4A (Cont.)

AUDIT ENCRYPTION COUNTS

| NAME | DESCRIPTION | FORMAT | VALID VALUES | COMMENTS |
|---|---|---|---|---|
| DATA SUPPLIER ID | UNIQUE IDENTIFIED ASSIGNED TO EACH DATA SUPPLIER USING THE DATA ENCRYPTION APPLICATION | 9(3) | UNIQUE VALUE | USED FOR FUTURE POTENTIAL DEBUGGING OR ENHANCE ENCRYPTION PROCESSES |
| EXECUTION TYPE | TYPE OF EXECUTION BEING PERFORMED BY IMS | X(1) | BLANK - ROUTINE EXECUTION R - RE-EXECUTION DUE TO PROCESSING ERROR D - PROCESS IDENTIFIED THE CURRENT FEED TO BE A DUPLICATE OF ONE ALREADY PROCESSED | USED TO TRACK AUDIT INFORMATION CORRECTLY IN THE EVENT IMS IS REQUIRED TO RE-EXECUTE THE DATA ENCRYPTION PROCESS DUE TO UNFORESEEN PROCESSING ERRORS. |
| DATA SUPPLIER PROCESSING DATE | UNIQUE CALENDAR DATE MATCHING THE PROCESSING DATE ATTRIBUTE RECEIVED FROM THE DATA SUPPLIER | 9(8) | UNIQUE / VALID CALENDAR DATE | COPIED FROM THE DATA SUPPLIER'S PROCESSING DATE RECEIVED BY IMS. USED TO VALIDATE THAT IMS ONLY ENCRYPTED THE RECORDS PRODUCED. |
| IMS PROCESSING DATE | UNIQUE CALENDAR DATE BASED ON WHEN IMS PROCESSED THE DATA SUPPLIER'S RECORD | 9(8) | UNIQUE / VALID CALENDAR DATE | ONE RECORD WILL BE STORE FOR EACH CALENDAR DATE IN WHICH THE IMS DATA ENCRYPTION APPLICATION CONDUCTED PROCESSING |
| RECORD RECEIVED COUNT | COUNT OF RECORDS SUCCESSFULLY RECEIVED BY THE IMS DATA ENCRYPTION APPLICATION | 9(8) | INITIALIZED TO ZERO | 1 IS ADDED TO THE COUNTER EACH TIME A RECORD IS SUCCESSFULLY RECEIVED BY THE IMS DATA ENCRYPTION APPLICATION |
| RECORD UN-ENCRYPTED COUNT | COUNT OF RECORDS PROCESSED THROUGH THE DATA SUPPLIER DECRYPTION PROCESS | 9(8) | INITIALIZED TO ZERO | 1 ADDED TO COUNTER EACH TIME A RECORD IS DECRYPTED WITHIN THE IMS ENCRYPTION APPLICATION |
| RECORD IMS ENCRYPTED COUNT | COUNT OF RECORDS PROCESS THROUGH THE IMS LONGITUDINAL ENCRYPTION PROCESS | 9(8) | INITIALIZED TO ZERO | 1 ADDED TO COUNTER EACH TIME A RECORD IS ENCRYPTED USING THE IMS ENCRYPTION KEY WITHIN THE IMS DATA ENCRYPTION APPLICATION |
| RECORD RELEASED COUNT | COUNT OF RELEASED FROM THE IMS DATA ENCRYPTION PROCESS | 9(8) | INITIALIZED TO ZERO | 1 ADDED TO COUNTER EACH TIME A RECORD IS RELEASED FROM THE IMS DATA ENCRYPTION APPLICATION |

FIG. 5A

IMS DATA ENCRYPTION AUDIT REPORT FORMAT BY DAY

START DATE          CCYYMMDD
END DATE            CCYYMMDD
SUPPLIER ID         123
AGGREGATION LEVEL   BY DAY
FORMAT              PRINTED REPORT

| DATA SUPPLIER ID | DATA SUPPLIER PROCESSING DATE | IMS PROCESSING DATE | EXECUTION TYPE | RECORD RECEIVED COUNT | RECORD UN-ENCRYPTED COUNT | RECORD IMS ENCRYPTED COUNT | RECORD RELEASED COUNT |
|---|---|---|---|---|---|---|---|
| 123 | 2/3/2004 | 2/5/2004 | NORMAL | 5000 | 5000 | 5000 | 5000 |
| 123 | 2/4/2004 | 2/6/2004 | NORMAL | 1500 | 1500 | 1500 | 1500 |

FIG. 5C

- OTHER FORMATS / FILES

VALID INPUT CHARACTERS
THE FOLLOWING IS THE SET OF ALL CHARACTERS THAT WILL BE ACCEPTED BY THE APPLICATION AS VALID INPUTS. CHARACTERS OTHER THAN THIS WILL NOT BE TAKEN UP FOR THE INPUT PROCESSING.

ALPHANUMERIC CHARACTERS
A TO Z
a TO z
0 AND 1 TO 9

SPECIAL CHARACTERS
ACUTE - Á, á, É, é, Í, í, Ó, ó, Ú, ú, Ý, ý

GRAVE - À, à, È, è, Ì, ì, Ò, ò, Ù, ù

TILDE - Ã, ã, Ñ, ñ, Õ, õ

UMLAUT/DIAERESIS - Ä, ä, Ë, ë, Ï, ï, Ö, ö, Ü, ü

CIRCUMFLEX - Â, â, Ê, ê, Î, î, Ô, ô, Û, û, Ç, ç

HIPAA ZIP CODE REFERENCE FILE ─601

| NAME | DESCRIPTION | FORMAT | VALID VALUES | COMMENTS |
|---|---|---|---|---|
| HIPAA LOW POPULATION ZIP CODE | 3 DIGIT ZIP CODE WHERE THE PATIENT POPULATION IS UNDER 20,000 INDIVIDUALS | 9(3) | UNIQUE NUMBER | 14 3-DIGIT ZIP CODES CURRENTLY UNDER 20,000 INDIVIDUALS |

FIRST NAME STANDARDIZATION FILE ─602

| NAME | DESCRIPTION | FORMAT | VALID VALUES | COMMENTS |
|---|---|---|---|---|
| ORIGINAL FIRST NAME | COMMON NAME OFTEN AND ABBREVIATION OF A FULL FORMAL NAME | X(12) | TEXT | NAME NEEDING STANDARDIZATION (FOR EXAMPLE "BOB") |
| STANDARD FIRST NAME | STANDARD NAME FOR THE ORIGINAL FIRST NAME CONTENTS | X(12) | TEXT | STANDARDIZED NAME (FOR EXAMPLE "ROBERT") |

FIG. 6

MULTI-SOURCE LONGITUDINAL PATIENT-LEVEL DATA ENCRYPTION PROCESS

CROSS REFERENCE TO RELATED APPLICATIONS

This application claims the benefit of U.S. provisional patent application Ser. No. 60/568,455 filed May 5, 2004, U.S. provisional patent application Ser. No. 60/572,161 filed May 17, 2004, U.S. provisional patent application Ser. No. 60/571,962 filed May 17, 2004, U.S. provisional patent application Ser. No. 60/572,064 filed May 17, 2004, and U.S. provisional patent application Ser. No. 60/572,264 filed May 17, 2004, all of which applications are hereby incorporated by reference in their entireties herein.

BACKGROUND OF THE INVENTION

The present invention relates to the management of personal health information or data on individuals. The invention in particular relates to the assembly and use of such data in a longitudinal database in manner, which maintains individual privacy.

Electronic databases of patient health records are useful for both commercial and non-commercial purposes. Longitudinal (life time) patient record databases are used, for example, in epidemiological or other population-based research studies for analysis of time-trends, causality, or incidence of health events in a population. The patient records assembled in a longitudinal database are likely to be collected from a multiple number of sources and in a variety of formats. An obvious source of patient health records is the modern health insurance industry, which relies extensively on electronically-communicated patient transaction records for administering insurance payments to medical service providers. The medical service providers (e.g., pharmacies, hospitals or clinics) or their agents (e.g., data clearing houses, processors or vendors) supply individually identified patient transaction records to the insurance industry for compensation. The patient transaction records, in addition to personal information data fields or attributes, may contain other information concerning, for example, diagnosis, prescriptions, treatment or outcome. Such information acquired from multiple sources can be valuable for longitudinal studies. However, to preserve individual privacy, it is important that the patient records integrated to a longitudinal database facility are "anonymized" or "de-identified".

A data supplier or source can remove or encrypt personal information data fields or attributes (e.g., name, social security number, home address, zip code, etc.) in a patient transaction record before transmission to preserve patient privacy. The encryption or standardization of certain personal information data fields to preserve patient privacy is now mandated by statute and government regulation. Concern for the civil rights of individuals has led to government regulation of the collection and use of personal health data for electronic transactions. For example, regulations issued under the Health Insurance Portability and Accountability Act of 1996 (HIPAA), involve elaborate rules to safeguard the security and confidentiality of personal health information. The HIPAA regulations cover entities such as health plans, health care clearinghouses, and those health care providers who conduct certain financial and administrative transactions (e.g., enrollment, billing and eligibility verification) electronically. (See e.g., http://www.hhs.gov/ocr/hipaa). Commonly invented and co-assigned patent application Ser. No. 10/892,021, "Data Privacy Management Systems and Methods", filed Jul. 15, 2004, which is hereby incorporated by reference in its entirety herein, describes systems and methods of collecting and using personal health information in standardized format to comply with government mandated HIPAA regulations or other sets of privacy rules.

For further minimization of the risk of breach of patient privacy, it may be desirable to strip or remove all patient identification information from patient records that are used to construct a longitudinal database. However, stripping data records of patient identification information to completely "anonymize" them can be incompatible with the construction of the longitudinal database in which the stored data records must be linkable patient by patient.

Consideration is now being given to integrating "anonymized" or "de-identified". patient records from diverse data sources in a longitudinal database, where the data sources may employ different encryption techniques that can hinder or prohibit accurate longitudinal linking patient records. Attention is in particular directed to efficient processes for integrating multi-sourced longitudinal data in a manner that ensures the protection of an individual patient's privacy and complies with industry privacy regulations.

SUMMARY OF THE INVENTION

The present invention provides systems and processes for assembling de-identified patient data records in a longitudinal database. An object of the present invention is to provide processes for encrypting multi-sourced patient data records to overcome data source variances in individual encryption techniques and in the content of data records. The present systems and processes allow de-identified data records received from multiple data sources or suppliers to be assembled in a longitudinal database for market research and other analysis. The inventive systems and processes ensure patient privacy consistent with industry and other regulations concerning patient privacy.

An exemplary system for assembling the longitudinal database may include three sequential and tightly integrated components. A first component, which may be implemented at each of the multiple data source or vendor locations, is configured to perform critical data encryption of patient or healthcare data records generated or collected by the data source. Patient-identifying attributes in the data records are encrypted and coded in these processes. The patient-identifying attributes may be encrypted using two or more suitable encryption keys. Each attribute is encrypted using a longitudinal encryption key that only resides at the data source location and a second data source specific encryption key unique to each data source involved in the encryption process. Prior to encryption, the process standardizes the input data to ensure consistent encryption. The encrypted data records are transmitted securely to a common "central facility," which may receive data records from multiple data sources or vendors for assembly in the longitudinal database.

A second component of the exemplary system is implemented at the common central facility, which receives encrypted data records from the multiple data source or vendor locations. The various data sources or vendors may have encrypted the transmitted data records differently using the longitudinal encryption key and the data source specific encryption key. Accordingly, the second system component is configured to further process the received data records into standard encrypted formats. This process includes partial decryption of the data source specific encryption to a longitudinally encrypted level, and may further include re-encryption of the received data records using a "central facility" encryption key (e.g., a token-based key) to add an additional layer of encryption protection on the data before use. The data records are processed at the second component into a common encrypted format that allows the data records to be linked longitudinally (at the third system component). The second component processes are designed to be irreversible so that the processed data record attributes or fields cannot be decrypted under any circumstance to reveal the original patient-identifying attribute values.

A third and final system component, which also may be implemented at the central facility or other convenient longitudinal database facility, assembles the processed data records in the longitudinal database. This component applies matching algorithms, which may configurable according to data source specifics, against the processed data to determine suitable fictitious or pseudo "longitudinal patient" identifiers which can be used to label or tag the encrypted data records (processed at the second component). The two-component encrypted data records may, for example, be associated or tagged with a unique de-identified central facility "Longitudinal Patient Identifier, (LI)". Suitable statistical matching algorithms, which may be customizable, are employed to associate the LIs with the encrypted data records. The LIs can be used to link the respectively tagged data records longitudinally—i.e. LI by LI, to assemble the longitudinal database.

The longitudinal databases, which are assembled by the inventive system and processes, may address pharmaceutical and healthcare industry demand for multi-sourced longitudinal data analysis while protecting individual patient privacy. The inventive data encryption processes using multiple encryption keys, allow data sources (suppliers or vendors) to provide patient-level data to a longitudinal database facility, without fear of compromising HIPAA regulations or other privacy requirements. In addition, the inventive two-component encryption processes restrict the ability of a user or intruder to discover the identity of any individual patient from the encrypted data records. Thus, a longitudinal database facility can safely analyze data records received from multiple, independent data sources without risk of breaching individual patient privacy.

Further features of the invention, its nature and various advantages will be more apparent from the accompanying drawing and the following detailed description.

BRIEF DESCRIPTION OF THE DRAWINGS AND APPENDICES

FIGS. 2a-2d illustrate exemplary data supplier input and output file formats conforming to software applications that are used to process patient data records, in accordance with the principles of the present invention.

FIG. 3 illustrates exemplary structure and formats of various encryption keys deployed in the software applications for processing patient data records, in accordance with the principles of the present invention.

Figure 4B:
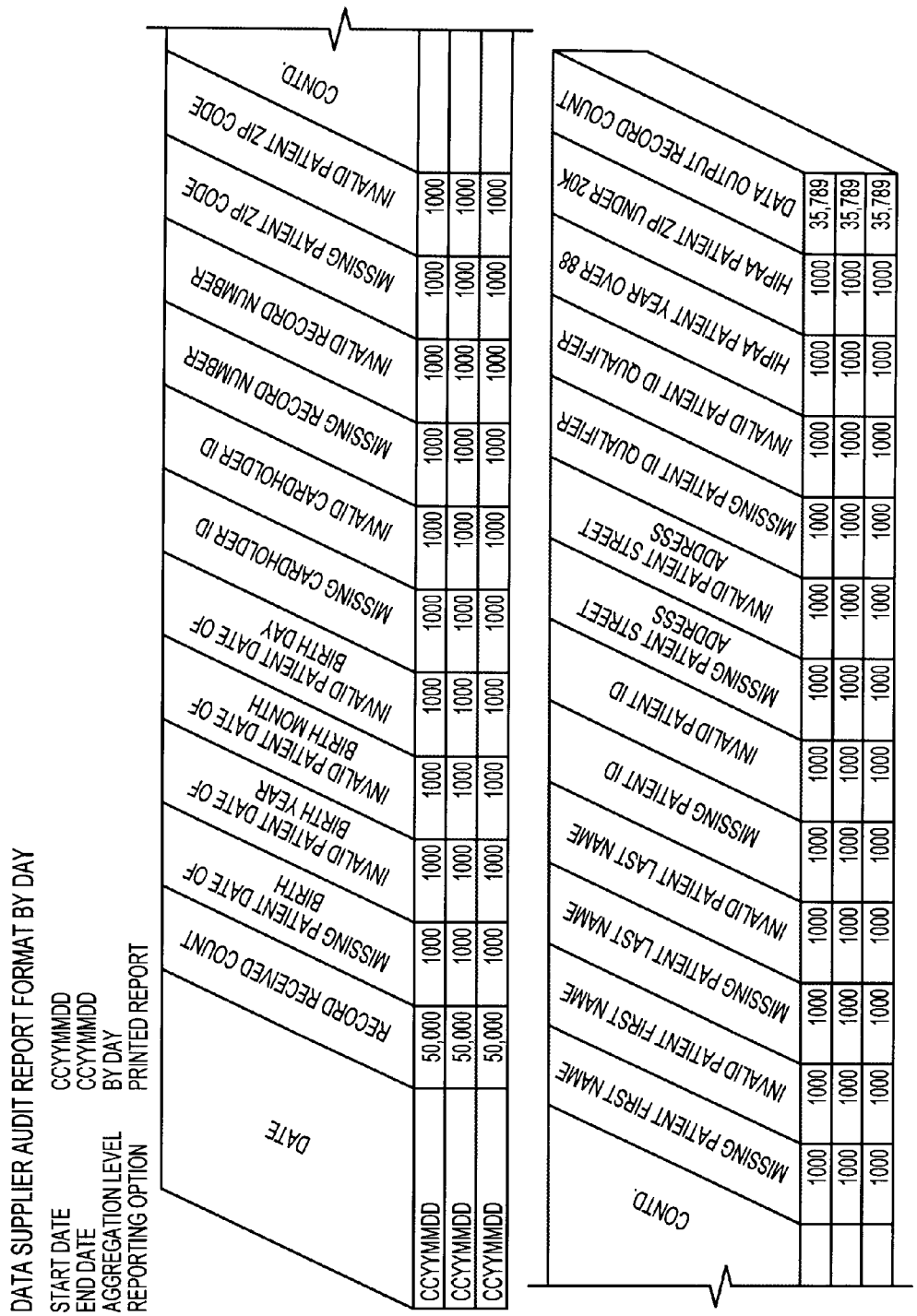
Figure 4C:
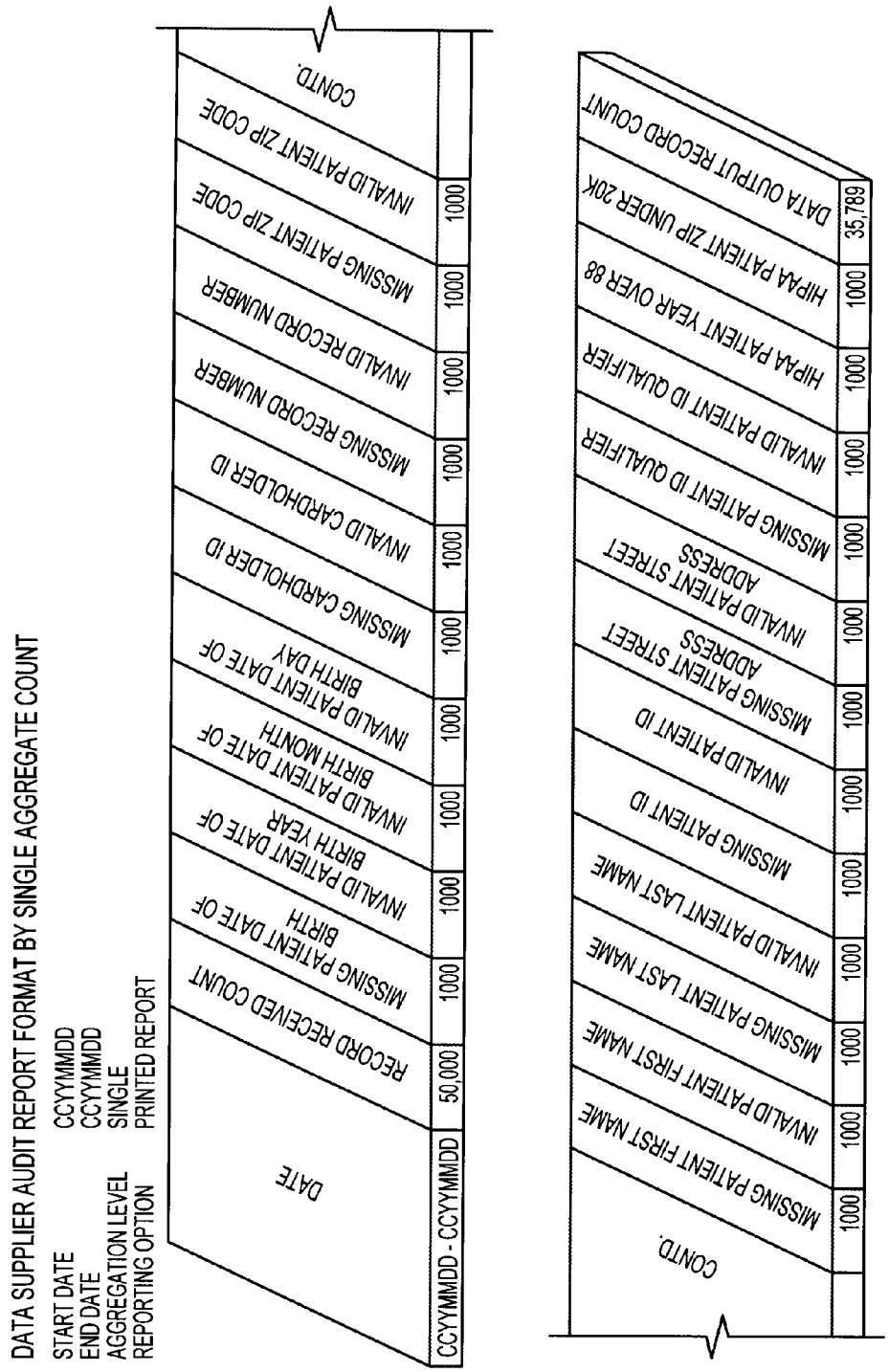

FIGS. 4a-c illustrate exemplary data source audit file formats and audit reports generated by the software applications for processing patient data records, in accordance with the principles of the present invention.

Figure 5B:
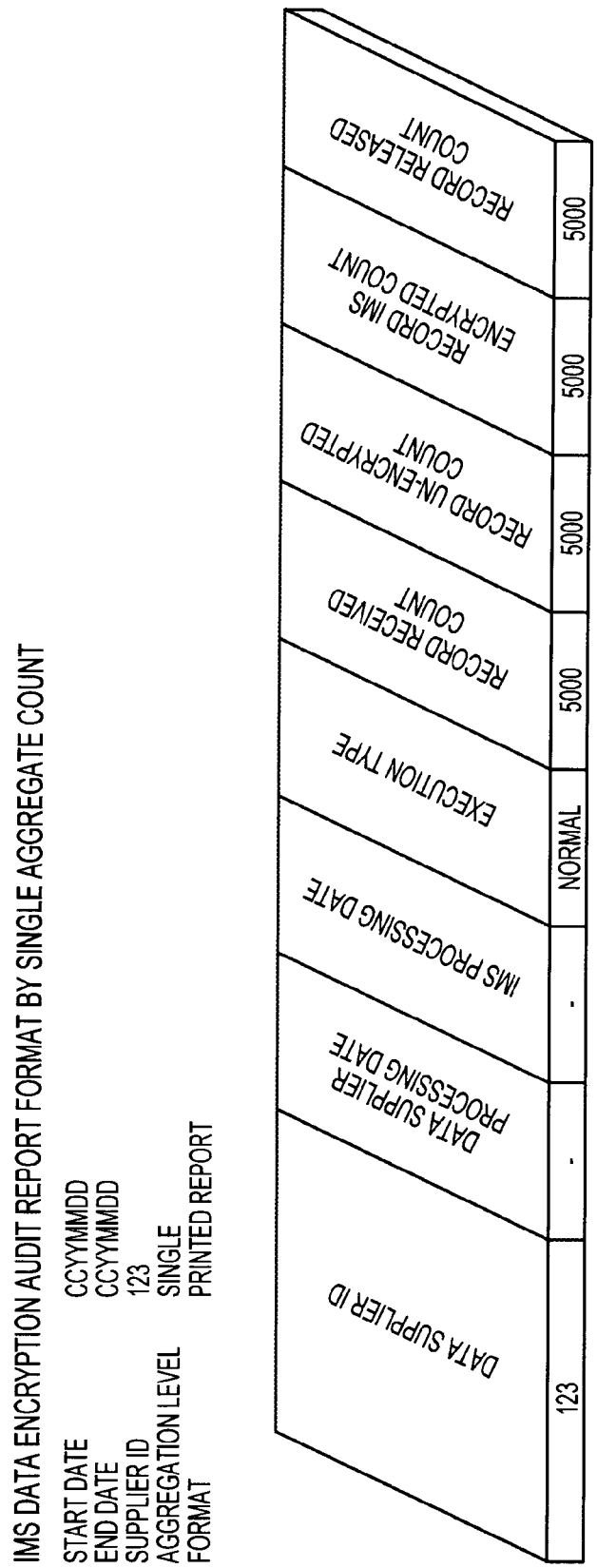

FIGS. 5a-c illustrate exemplary audit file formats and audit reports generated by the software applications for processing patient data records, in accordance with the principles of the present invention.

FIG. 6 illustrates exemplary formats for some characters and standardized data fields in files that are processed by the software applications, in accordance with the principles of the present invention.

While the present invention will now be described in detail with reference to the FIGS., it is done so in connection with the illustrative embodiments.

DETAILED DESCRIPTION OF THE PREFERRED EMBODIMENTS

The present invention provides solutions for integrating patient data records, which may be acquired from multiple sources into a longitudinal database. The patient data records are integrated into the longitudinal database, at least on a statistical basis, individual patient-by-patient, without any risk of breaching of any individual patient's privacy.

An exemplary solution involves multiple data processing steps in which patient data records are encrypted at least twice using multiple encryption keys. The solution may be implemented in a data processing system, which spans or involves one or more entities (e.g., a data source, vendor or supplier ("DS"), a longitudinal database facility ("LDF"), a third party implementation partner ("IP"), and an encryption key administrator. The IP, who also may serve as the encryption key administrator, may be authorized to operate at a LDF component site.

At a first processing step of the solution, each DS prepares data records for secure transmission to the LDF. The DS standardizes and encrypts selected data fields (e.g., patient-identifying attributes and/or other standard attribute data fields) in the patient data records to convert the patient data records into a first "anonymized" format. Each DS uses two keys (i.e., a vendor-specific key and a common longitudinal key associated with a specific LDF) to doubly-encrypt the selected data fields. The doubly-encrypted data records are transmitted to the LDF component site, where the IP can further process the data records. The received data records are further processed at the LDF component site into a second anonymized format, which is designed to allow the data records to be linked (on a statistical basis) individual patient-by-patient without recovering the original unencrypted patient identification information. For this purpose, the doubly-encrypted data fields in the patient records received from a DS are partially decrypted using the specific vendor key (such that the doubly-encrypted data fields still retain the encryption by the common longitudinal key). A third key (e.g., a token based key) may be used to further prepare the now-singly encrypted (i.e. common longitudinal key encrypted) data fields for use in a longitudinal database. Longitudinal identifiers (IDs) or dummy labels that are internal to the LDF, may be used to tag the data records so that they can be linked individual ID by ID in the longitudinal database without knowledge of original unencrypted patient identification information. Statistical matching algorithms are used to associate the IDs with the data records.

Figure 1:
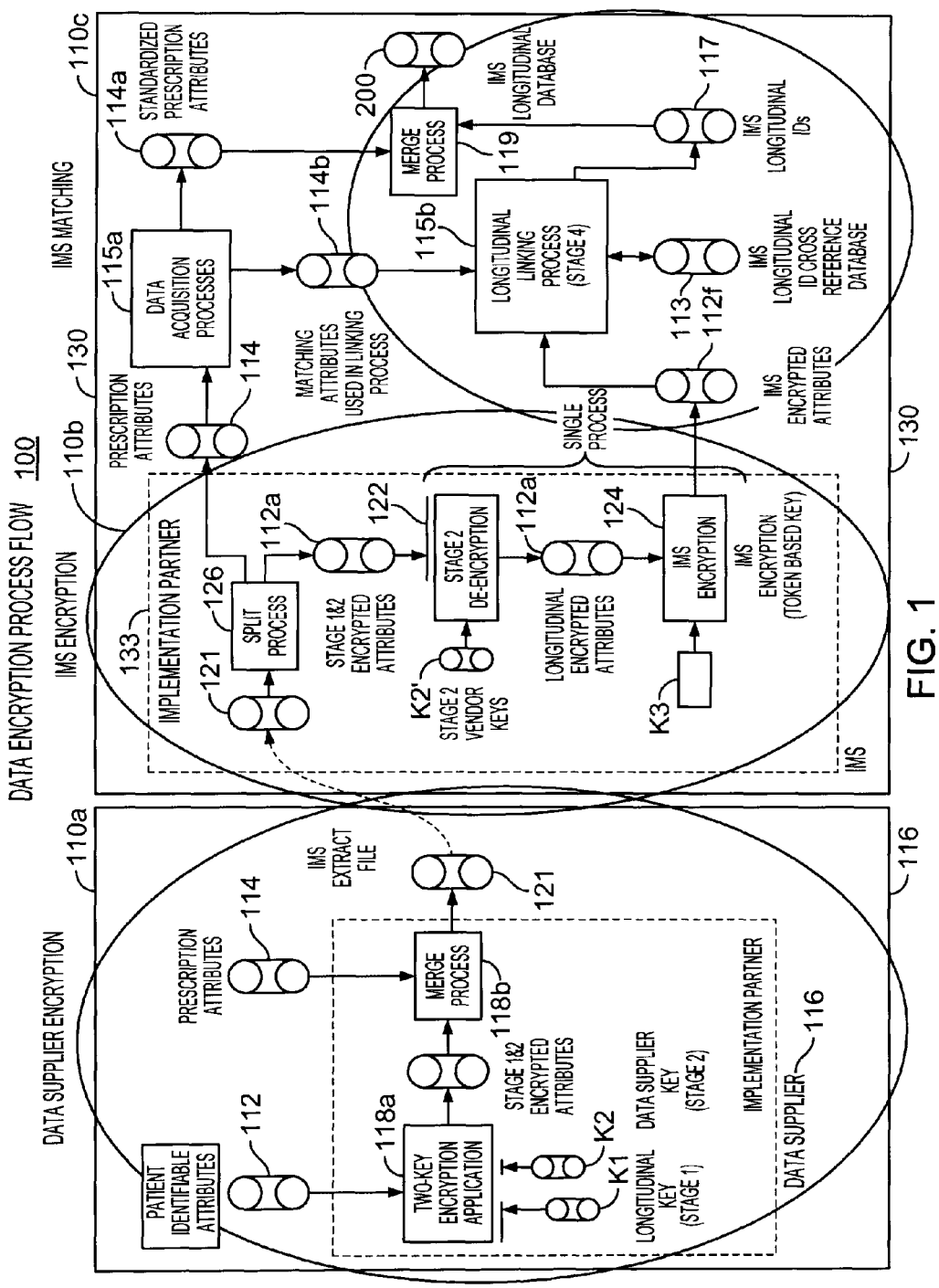
FIG. 1 is a block diagram illustrating system components and processes for assembling a longitudinal database from multi-sourced patient data records, in accordance with the principles of the present invention.

FIG. 1 shows components 110a, 110b and 110c of an exemplary data processing system 100, which may be used for assembling multi-sourced patient data records into a longitudinal database 200 at an longitudinal data base facility 130.

Component 110a relates to data processing activities at one or more data source locations 116 (e.g., data suppliers or vendors, pharmacies, hospitals, etc.) At these locations, raw transaction data records (e.g., patient prescription records) are prepared for transmission to a LDF. The raw data records may contain patient-identifying attributes 112 and other attributes (e.g., prescription attributes 114) that are non-identifying information. Component 110a includes a two-key encryption application, which is used to doubly-encrypt and code patient-identifying attributes 112 in the raw data records. This double-encryption may be accomplished using a longitudinal facility encryption key "K1" and a data supplier's private encryption key "K2". The resulting doubly-encrypted data attributes 112e are merged with corresponding prescription attributes 114 in the data records by a suitable merging application (e.g., application 118b). The merged data records may be assembled as doubly-encrypted data records in a data file 121 or other form suitable for secure transmission to longitudinal database facility (e.g., LDF 130).

Components 110b and 110c relate to data processing activities at LDF 130. Component 110b is configured to remove data source specific characteristics from the data record. This may be achieved, for example, by partial decryption of the doubly-encrypted data attributes in a data record received from an individual data source. A suitable decryption application 122 is included for this purpose in component 110b. The data records in file 121 received at LDF 130 are first processed by a split process application 126 to separate prescription attributes 114 from the doubly-encrypted data attributes 112e. The doubly-encrypted data attributes 112e are then processed by decryption application 122. Decryption application 122 may use a public key K2' (which is complementary to the data supplier's private encryption key K2) to partially decrypt the doubly-encrypted data attributes 112e, and thereby recover singly-encrypted data attributes 112a. The singly-encrypted data records correspond to raw data record attributes that are singly encrypted by longitudinal facility encryption key K1. Component 110b also may include another encryption application 124 to further encrypt the now singly-encrypted data attributes 112a in a manner specific to particular LDF 130. Encryption application 124 may, for example, use a token-based key K3 to encrypt data attributes 112a to generate LDF-encrypted attributes 112f.

Component 110c at LDF 130 includes a data acquisition process 115a, which issued to segregate prescription attributes 114 into two categories (1) a set of standardized prescription attributes 114a, and (2) a set of matching attributes 114b. The latter attributes may be used in a linking process application 115b by which encrypted data records 112f are associated with or assigned unique longitudinal patient identifiers (IDs). Component 110c also may include a longitudinal ID cross-reference table or database 113, which can be referenced by application 115b during the assignment process. Cross-reference database 113 may include a list of IDs and sets of corresponding data attribute values. Linking process application 115b may include suitable matching algorithms, which assign unique longitudinal patient identifiers (IDs) to the encrypted data records on a statistical and/or deterministic basis by matching attributes in the encrypted data records with reference attribute values. Exemplary matching algorithms are described in coinvented and co-pending U.S. patent application Ser. No. 11/122,565, filed on May 5, 2005. The assigned IDs may be stored in a ID database 117. Component 110c may further include a merge process application 119, which merges standardized prescription records 114a by assigned IDs 117 into a longitudinal database 200.

The probabilistic and/or deterministic matching algorithms of linking process application 115b are designed to utilize only a small set of encrypted patient-identifying data attributes for effective assignment of a longitudinal patient identifier (ID). In an exemplary implementation, the assignment of a longitudinal patient identifier (ID) may be based on a select set of a few encrypted patient-identifying data attributes (e.g., up to only eight attributes such as a patient's date of birth, cardholder identification, record number, zip code, first name, last name, street address, and an industry standard patient identifier. The industry standard patient identifier may, for example, be a patient identifier according to the National Council for Prescription Drug Programs (NCPDP) standards).

The selected set of data attributes in a data record may be first placed in a standard format using any suitable standardization algorithm and then stored, for example, in database or file 112. The selected set of data attributes is then twice encrypted using a two-key encryption application 118a, which includes a longitudinal encryption key K1 and vendor specific encryption key K2. In particular, each data attribute in the selected set is independently encrypted twice at the data source 116. First, the universal longitudinal encryption key K1 (which is available only at data suppler sites but not at LDF 130) is used to encrypt the data attributes. Then, the vendor specific key K2, is used to again encrypt the data attributes. The set of twice-encrypted data attributes and the prescription attributes in the data record are transmitted to LDF 130 in a suitable electronic file (e.g., in file 121).

LDF 130 may arrange with a third party implementation partner (IP) to assist data suppliers or sources in defining and implementing the acquisition, encryption and transmission processes. Further, LDF 130 may include a secure processing environment 133 to receive and process the transmitted data file 112. Secure processing environment 133 may be accessible only to the third party IP, to minimize or avoid the risk of breach of patient privacy by LDF personnel or processes. The secure processing environment 133 may include a list of the vendor specific keys K2-K2' corresponding to all data sources involved in supplying data to LDF 130. These keys may be used by the IP to partially decrypt the twice encrypted set of data attributes in secure processing environment 133. Secure processing environment 133 also may include suitable counting processes to account for and audit records for each data source 116. Similar counting processes may be conducted in components 110b and 110c to provide traceable audit records of all activities. The traceable audit records may be useful for identifying and resolving data quality issues that may occur.

In another view, the present invention can be described from a perspective of software implementations of data processing system 100. Various software applications may be utilized in components 110a-110c of data processing system 100 to conduct different data processes (e.g., processes 118a, 118b, 122, 124, 126, 115a, 115b, and 119). The software applications may be designed so that the processes can be operated individually or separately by the following primary parties: a LDF, various data suppliers who communicate various healthcare transactions to the LDF, a key administrator responsible for generation and management of encryption keys used at both the data suppliers' and LDF's environments, and an implementation partner (IP) who may be responsible for installation/maintenance of the execution environments. The IP and the key administrator may be the same party.

The separate software applications may be designed to meet specific private initiative privacy standards, government regulations, and industry standard data formatting requirements. The separate software applications are operated in a integrated manner (referred to herein collectively as the "Software System") across data processing system 100.

The Software System and its applications provide various functions at various stages of steps in the inventive double encryption/matching solution for constructing a longitudinal database with formatted data records. The functions may be called or operated by an authorized user (e.g., one or more of the four parties: LDF, DS, IP and/or key administrator).

The Software System through its encryption applications, enables multiple data suppliers to provide an LDF with data records that have patient attributes in an industry accepted secure encrypted format. The encrypted attributes are in placed in a format that enables the LDF to link multi-sourced transaction records by individual. The format of the encrypted attributes is such that it does not allow the LDF to learn the identity of the individual(s). However, the format allows the LDF to link the records by individual using suitable statistical matching applications without having to learn any individual's identity. The Software System also may include other applications or routines for performing other functions, e.g., standardizing data, reformatting or acquiring data attributes, and generating audit counts or audit reports The Software System includes at least a LDF encryption application and a DS encryption application, and at least one key administration (IP) application. The DS encryption application may include one or more routines that are designed to acquire data records or attributes, standardize the data attributes including HIPAAtization of data attributes if requested, and doubly encrypt patient-identifying information. The DS encryption application may include routines for creating encryption keys and to encrypt the encryption keys. A secure storage is provided for the encryption keys. The DS application also may include routines for auditing and secure auditing data management (audit data to be written to a file), and audit reporting. Further, the application also may include routines for reference file integration (HIPAA, zip codes/first name standardization file etc.).

The LDF encryption application allows decryption and encryption of data supplier's encrypted attributes using a data supplier key and a LDF encryption key, respectively. A secure storage is provided for the encryption keys. The LDF application also may include routines for auditing and secure audit data management (e.g., writing audit data to a file), and audit reporting. Secure audit data management advantageously allows parties (e.g., a LDF) to demonstrate or verify that the audit files have not been modified. Secure auditing data management may include the capability to detect modification and/or tampering of the audit files or reports. The LDF application may be deployed on suitable hardware security modules (e.g., an nCipherHSM).

The key administration application may include routines for generation of encryption keys, a solution for secure storage solution for encryption keys, and processes for deploying the encryption keys to data suppliers, LDF, and IP. FIG. 3 shows exemplary formats and characteristics of the encryption keys (e.g., K1, K2 and K3).

In an implementation of the Software System, the software applications and encryption keys may be installed by the three parties (DS, LDF and IP) by themselves or with the help of external technical support. The Software System may be designed to be operate on a variety of hardware or software environments or platforms. The data supplier applications, in particular, may be designed to be operated to be deployed across a variety of platforms that are in common use. The reporting routines in the applications may involve customized GUIs. The applications may include subroutines to fill in blanks (e.g., write a 'B' character to an attribute's data field) if the input data received has missing data fields (blank, spaces, zeros). Similarly, the applications may mark (e.g., write an 'I' character to an attribute's content) if the data fields received are invalid. (See e.g., FIG. 6).

The Software System may be configured so that the LDF will not have access to the LDF encryption application software, encryption keys, or any encryption hardware. In suitable implementations of the Software System, the LDF encryption application and keys may be maintained and operated in a secure hardware platform that can only be accessed using a smart card or other restricted access mechanism. A suitable hardware platform may be nCipher's nShield Hardware Security Module.

In preferred embodiments of the Software System, the encryption applications and other applications may be designed to be sufficiently generic to accept a variety of input file formats. For example, some data suppliers may choose to send the patient-identifying attributes and the non-identifying transaction attributes as a separate file, while other data suppliers may choose to send both together in a single file. The encryption applications may be designed to operate on either format. The individual data supplier file formats may be agreed upon by the data supplier and the LDF beforehand. Upon receipt of data from a data supplier, the LDF may map the received encrypted attributes into the LDF Data Encryption application's standard format. Since common data suppliers usually provide data files that contain the transaction data and patient data in the same record, separation/merging of encrypted and unencrypted data attributes is not necessary and may be optional in most instances. The Software System applications may be configured so that data attributes that need to be encrypted are acquired and encrypted, and then added to other non-encrypted transaction attributes at the end of a data record.

The data file, data record, and report formats at input and/or output stages of various applications in the Software System may be standardized. The file or data records may, for example, have a defined structure with fixed length data fields. FIGS. 2*a-d* show exemplary formats for Data Encryption Application (DS) Input Record and Output Record, Data Encryption Application (LDF) Input File and Output Files. FIGS. 4*a*-4*c* show exemplary Data Supplier Audit file formats, and FIGS. 5*a-c* show exemplary LDF Audit file formats.

With reference to FIG. 2*a*, the data records in data supplier encryption input file 2001 may have a standardized fixed length, e.g., 1 to 634 bytes long. Each data field in an input data record is reserved for a designated data attribute (e.g., prescription or patient-identifying attribute). A select set of designated attributes may be intended for encryption (e.g., eight data fields at bytes 501-632, which contain sensitive private information such as patient's date of birth, zip code, etc.).

With reference to FIG. 2*b*, data supplier encryption output file 2002 shows encrypted versions of the selected set of eight designated attributes at bytes 512-923. Output file 2002 also contains attributes, which identify the data supplier and the date of processing (e.g., bytes 471-481). These attributes may be useful for audit or tracing purposes. Output file 2002 may contain optional attributes, which correspond to HIPAA versions of the patient zip code and birthdate, for example, at bytes 926-938.

With reference to FIG. 2*c*, the data records in LDF encryption input file 2003 include the data supplier encrypted set of eight designated attributes (at bytes 44-455). Input file 2003 also includes optional data fields identifying the gender of the patient (byte 1), a data supplier identifier (bytes 2-5), a processing date (bytes 6-13) and matching attributes (bytes 14-43). The matching attribute data fields may be used to store suitable parameters (e.g., ID) that can be used to match encrypted attribute contents back to a data supplier's unique transaction attributes. FIG. 2d shows the format of an exemplary output file 2004 in which the set of the data supplier encrypted set of eight designated attributes (in file 2003) have been further encrypted by the LDF encryption application (e.g., a token based application).

The System Software and its applications provide various functions at various stages of the inventive double encryption/matching solution for constructing a longitudinal database with formatted data records. The functions may be called or operated by an authorized user (i.e., one or more of the involved parties, LDF, DS or IP/key administrator). The Software System may include specific functions for acquiring data attributes, standardizing data attributes, making the data HIPAA Privacy compliant, and encrypting the data attributes, and requesting audit count reports at a data supplier location (e.g., component 110a), and specific functions for acquiring data-supplier encrypted data attributes, and encrypting the data attributes and requesting audit count reports at an LDF location. The Software System also may include specific functions for key administration, key security, and audit storage. Exemplary properties and features of the various functions of a System Software configuration are shown in tabular form in Appendices A-K.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

APPENDIX A

| | Data Supplier Encryption Function: Acquire Data Attributes |
| --- | --- |
| Summary | The operational processes at the data supplier end acquire the required attributes (that are to be encrypted /standardized) from the data supplier's data sources and convert them into a format that is accepted by the encryption process. |
| Primary Actor(s) | Data Supplier, Implementation Partner |
| Secondary Actor(s) | None |
| Pore-conditions | Configuration file containing:<br>　The list of attributes (and offsets) that are sent as input to the<br>　encryption application<br>　The configuration parameters required by the application. |
| Post-conditions | The input data attributes are passed to the standardization and HIPAA privacy compliance process |
| Exceptions | Error message encountered will be written to the command line and application log file |
| Dependent Use Case | N/A |
| Description | 1. The encryption application will analyze the configuration file and understand<br>　1.1. Record type where the encrypted information exists<br>　(Some data supplier provide multiple record types in one<br>　file. For example a header, footer and detail record). The<br>　process will only utilize the record e indicated b this<br>　parameter.<br>　1.2. Input/Output file format like name of the attribute that<br>　will be sent in with their start and end positions from<br>　beginning of record.<br>　1.3. Gender standardization request - If the data supplier<br>　requests for gender standardization this value is set to "yes<br>　1.4. DOB Format indicators as given below<br>　　A - CCVYMMDD<br>　　B - MMDDCCYY<br>　　C - MM/DD/CCYY<br>　　D - CCYY/MM/DD<br>　1.5. Patient Gender Format indicators as given below<br>　　A - (M = Male, F = Female, O = Other)<br>　　B - (1 = Male, 2 = Female, 3 = Unspecified)<br>　1.6. HIPAA attributes - If HIPAA attributes are requested<br>　by the data supplier, the encryption application should<br>　produce the HIPAAtized value of patient zip code and<br>　patient date of birth.<br>　1.7. Data supplier ID<br>　1.8. Location of data supplier longitudinal key file and<br>　data supplier encryption key file.<br>　1.9. Location of input and output data feed file.<br>　1.10. Location of First Name Standardization file<br>　1.11. Location of HIPAA zip code reference file<br>　1.12. Location of Audit and secure audit file<br>The following kinds of scenarios should be handled by the acquire attributes section.<br>　1. Data Supplier Feed format file as in Appendix A<br>　2. Format file with no transactional information and only<br>　patient information as in Appendix A.<br>　3. Feed format file with no transactional information and<br>　selective patient information.<br>　4. Feed file with selective patient information |

APPENDIX B

| | Data Supplier Encryption Function: Standardize Data Attributes |
|---|---|
| Summary | The operational processes at the data supplier end acquire the required attributes (that are to be encrypted / standardized) from the data suppliers data sources and convert them into a format that is accepted by the encryption process. These attributes are then subject to standardization process. |
| Primary Actor(s) | Application processes that acquire data attributes, Standardize Attributes process a (application process) |
| Secondary Actor(s) | Implementation Partner, Data Supplier |
| Pre-conditions | 1. Data attributes to be encrypted/standardized have been acquired by the 'Acquire Attribute' process and is made available to the encryption application<br>2. Patient Gender standardization parameter is set-up for the data supplier<br>3. Record Number standardization parameter is set-up for the data supplier.<br>4. Attribute mapping (where attributes reside in the input file) has been set up |
| Post-conditions | The input data attributes are standardized and passed into the HIPAA privacy compliance process |
| Exceptions | No exception messages. All errors are recorded in the Audit Encryption Record counts Table |
| Dependent Use Case | |
| Description | Attributes are passed into the Standardize Data Attributes process<br>Process will standardize the Patient Date of Birth Attribute as follows:<br>2.1. If Patient Date of Birth Format Indicator equals "B, "C or "D", the application will convert the date into indicator "A"format (CCYYMMDD)<br>2.2. If the Patient Date of Birth Format Indicator does not equal "A" or "B" or "C" or "D" then the encryption application will cease processing, inform the administrator and terminate. No records will be processed.<br>2.3. If the Patient Date of Birth attribute is missing (blank, spaces or zeros), 1 will be added to the Missing Patient Date of Birth count and 'B' will be written to the attributes contents. All other Patient Date of Birth validation will be skipped.<br>2.4. If the year is not valid (valid if age of the patient is less than or equal to 150 years or if the patient's year of birth is less than +1 year from the current year), 1 will be added to the invalid Patient DOB Year count and 'I' written to the Patient Date of Birth attribute. All other Patient Date of Birth validation steps will be skipped.<br>2.5. If the month is not valid (valid if between 1 and 12), 1 will be added to the invalid Patient DOB Month count and 'I' is written to the Patient Date of Birth attribute. All other Patient Date of Birth validation steps will be skipped.<br>2.6. If the Day is not valid (valid if between 1 and 31), 1 will be added to the invalid Patient DOB Day count and 'I' is written to the Patient Date of Birth attribute.<br>2.7. A check is also made to ensure that the day value does not exceed the maximum value for a month. If the month day combination is not valid (including February in a Leap year), 1 will be added to the invalid patient DOB count and "I" is written to the Patient Date of Birth attribute. All other DOB validations steps will be skipped.<br>Process will standardize the Patient Gender Attribute<br>3.1. Job accepts the Patient Gender Input Parameter prior to execution<br>    3.1.1. If the Patent Gender input parameter indicates the need to be standardized the patient gender the following steps are executed. Otherwise, the Patient Gender is skipped in the process and no output is produced.<br>3.2. If Patient Gender Format Indicator equals "A", the application will convert the Gender attributes contents into indicator "B" format (1=Male, 2=Female, 3=Unspecified). The Patient Gender Format Indicator will be configured by the implementation partner and available in a configuration file.<br>3.3. If the Patient Gender Format Indicator does not equal "A" or "B" the encryption application will cease processing, inform the administrator and terminate. No records will be processed. |

APPENDIX B-continued

Data Supplier Encryption Function: Standardize Data Attributes

3.4. If the Patient Gender is missing (if blank or space), 1 will be added to the Missing Patient Gender count and 'B' is written to the Patient Gender attribute. All other Patient Gender validation steps will be skipped.
    3.5. If the Patient Gender is not valid (valid if 1, 2, 3), 1 will be added to the invalid Patient Gender Count and 'I' is written to the Patient Date of Birth attribute
  Process will standardize the Cardholder Id Attribute
    4.1. Data contents will be left justified.
    4.2. Leading zeros and spaces will be removed. Remaining contents left justified
    4.3. All special symbols (-*&I\\][{}::'.,<") will be removed. Remaining contents left justified to fill gaps
    4.4. Remaining right most bytes space filled
    4.5. If the Cardholder Id is missing (all blanks, spaces, zeros), 1 will be added to the Missing Cardholder Id count and 'B' is written to the Cardholder Id attribute. All other Cardholder Id validation will be skipped.
    4.6. If the Cardholder Id is invalid (all one character or one number, e.g. 11111111 or aaaaaaaa), 1 will be added to the Invalid Cardholder Id count and 'I' is written to the Cardholder Id attribute.
    4.7. All contents will be standardized to all upper case to make sure that the encrypted values are same for comparison.
  Process will standardize the Record Number
    5.1. Job accepts the Record Number Input Parameter prior to execution
        5.1.1. If the Record Number input parameter indicates the need to standardized the Record Number the following steps are executed. Otherwise, the Record Number is skipped in the process and no output is produced.
    5.2. Data contents will be left justified
    5.3. Leading zeros and spaces will be removed. Remaining contents left justified
        5.3.1. Leading zeros in a Record Number will be stripped off uniformly across data suppliers for standardization purposes even if they are a valid piece of the record number.
    5.4. All special symbols (-*&I\\][{}::'.,<") will be removed. Remaining contents left justified to fill gaps
    5.5. Remaining right most bytes space filled
    5.6. If the Record Number is missing (all blanks, spaces, zeros), 1 will be added to the Missing Record Number count and 'B' is written to the Record Number attribute. All other Record Number validation will be skipped.
    5.7. If the Record Number is invalid (all one character or number), 1 will be added to the Invalid Record Number count and 'I' is written to the Record Number attribute.
    5.8. Contents will be standardized to all upper case
  Process will standardize the Patient Zip Code
    6.1. If the Patient Zip Code is missing (all blanks, zeros), 1 will be added to the Missing Patient Zip Code count and 'B' is written to the Patient Zip Code attribute. All other Patient Zip Code validation will be skipped.
    6.2. If the Patient Zip Code is invalid Patient Zip Code count and 'I' is written to the Patient Zip Code attribute. All other Patient Zip Code validation will be skipped. A Patient Zip Code will be invalid if it contains Contains one or more special characters
  Process will standardize the Patient Name
    7.1. For the Patient First Name and Patient Last Name attributes the following standardization will be performed (Refer to Appendix D for valid input character list)
        7.1.1. Data contents will be left justified
        7.1.2. Leading zeros, blanks and spaces will be removed. Remaining contents left justified
        7.1.3. All special symbols (-*&"\][{}::'.,<") will be removed. Remaining contents left justified to fill gaps
        7.1.4. Remaining right most bytes space filled
        7.1.5. Contents will be standardized to all upper case
    7.2. If the Patient First Name is missing (all blanks, zeros, spaces), 1 will be added to the Missing Patient First Name count and 'B' is written to the Patient First Name attribute. All other Patient First Name validations will be skipped.

APPENDIX B-continued

Data Supplier Encryption Function: Standardize Data Attributes 7.3. If the Patient Last Name is missing (all blanks, zeros, spaces), 1 will be added to the Missing Patient Last Name count and 'B' is written to the Patient Last Name attribute. All other Patient Last Name validations will be skipped 7.4. If the Patient First Name is invalid (all numbers, all the same character), 1 will be added to the Invalid Patient First Name count and 'I' is written to the Patient First Name attribute. All other Patient First Name validations will be skipped.

7.5. If the Patient Last Name is invalid (all numbers, all the same character), 1 will be added to the Invalid Patient Last Name count and 'I' is written to the Patient Last Name attribute. All other Patient Last Name validations will be skipped 7.6. The Patient First Name contents will be compared to the Common First Name field in the First Name Standardization file. If a match is found, the Standard First Name contents will be copied to the Patient First Name field Process will standardize the NCPDP Patient Id Attribute 8.1. If no NCPDP Patient Id Qualifier is provided in the input file, it should be assumed to contain "99" for the remainder of the processing 8.2. If the NCPDP Patient Id Qualifier Indicator does not equal "01", "02", "03", "04", "05", "99" or spaces then 1 is added to the Invalid Patient Id Qualifier count and 'I' is written to the Patient Id attribute. All other Patient Id validation steps are skipped.

8.3. For the NCPDP Patient Id attribute the following standardization will be performed:

8.3.1. Data contents will be left justified 8.3.2. Leading zeros, blanks and spaces will be removed. Remaining contents left justified 8.3.2.1. Leading zeros in a patient id will be stripped off uniformly across for standardization purposes for data suppliers even if they are a valid piece of the cardholder's id.

8.3.3. All special symbols (-*&I\\][{};:'.,<") will be removed. Remaining contents left justified to fill gaps 8.3.4. Remaining right most bytes spaced filled 8.3.5. Contents will be standardized to all upper case.

8.4. If the NCPDP Patient Id is missing (all blanks, zeros or spaces), 1 will be added to the Missing Patient Id count and 'B' is written to the Patient Id attribute. All other Patient Id validations will be skipped 8.5. If the NCPDP Patient Id is invalid (all the same numbers or all the same character), 1 will be added to the Invalid Patient Id count and 'I' is written to the Patient Id attribute. All other Patient ID validations will be skipped.

Process will standardize the Patient Street Address Attributes 9.1. Data contents will be left justified 9.2. Leading spaces will be removed. Remaining contents left justified 9.3. All special symbols (-*&/\\][{};:'.,<") will be removed. Remaining contents left justified to fill gaps 9.4. If the Patient Street Address is missing (all blanks, spaces, zeros), 1 will be added to the Missing Patient Street Address count and 'B' is written to the Patient Street Address attribute. All other Patient Street Address validation will be skipped.

9.5. If the Patient Street Address is invalid, 1 will be added to the Invalid Patient Street Address count and 'I' is written to the Patient Street Address attribute. Patient Street Address will be considered invalid if 9.5.1. Street Address does not contain any numbers 9.5.2. Contains more than 15 numeric digits in a row The process will read the Patient Street Address Attribute from left to right one digit at a time until a numeric value is found. The process continues reading until a non-numeric digit is found. The numeric value found from the starting and ending point will be written to the Patient Street Address attribute. For example if "1245 Main Street, Apartment 403" was provided, "1245" will be written to the Patient Street Address at the

APPENDIX B-continued

Data Supplier Encryption Function: Standardize Data Attributes conclusion of the Patient Street Address standardization process. The maximum number of digits to be accepted in a row will be 15.
Standardized Attributes are passed to the HIPAA Privacy Compliance process

APPENDIX C

Data Supplier Encryption Function: HIPAA Privacy Compliance

| | |
|---|---|
| Summary | After standardization, HIPAA privacy compliance process is invoked which creates HIPAA compliant attributes for Patient Date of Birth and Patient Zip Code attributes. This standardization process is only invoked if the data supplier requests for the same in the encryption application. |
| Primary Actor(s) | Standardize Attributes process (application process), HIPAA Privacy Compliance process a application process |
| Secondary Actor(s) | Implementation Partner, Data Supplier |
| Pre-conditions | All input attributes have been standardized by the Standardize Attributes application process |
| Post-conditions | HIPAA input parameter has been setup |
| Exceptions | A HIPAA compliant Patient Date of Birth and Patient Zip Code attributes are produced |
| Dependent Use Case Description | No exception messages. All errors are recorded in the Audit Encryption Record counts Table |

Jobs accepts the HIPAA input parameter prior to execution
1.1. If the HIPAA input parameter is set up to exclude the HIPAA processing the remainder of the steps are skipped.
Process accepts the Patient Date of Birth and Patient Zip Code attributes from the Standardize Attributes process
To create the HIPAA Patient Date of Birth attribute the following processes are performed against the Patient Date of Birth Field
3.1. For the HIPAA Patient Date of Birth attribute "01" is written to the Day and Month components of the date
3.2. For the HIPAA Patient Date of Birth Year component the year is copied from the Patient Date of Birth attribute
  3.2.1. If the Patient Date of Birth attribute contains 'B' or 'I' move "1800" to the HIPAA patient Date of Birth year
3.3. If the year of birth calculates to an age of over 88 years old, move "0000" to the HIPAA Patient Date of Birth year component.
  3.3.1. Add 1 to the HIPAA Patient Year Over 88 counter within the Audit Encryption Counts table
To create the HIPAA Patient Zip Code attribute the following processes are performed against the Patient Zip Code Attribute
4.1. If the Patient Zip Code is 'I' (invalid), move 'I' to the HIPAA Patient Zip Code
4.2. If the Patient Zip Code is 'B' (missing), move 'B' to the HIPAA Patient Zip Code
4.3. If the Patient Zip code is Valid (not missing or invalid)
  4.3.1. Move the Patient Zip Code to the HIPAA Patient Zip code
  4.3.2. Move "00" to the right most two digits of the HIPAA Patient Zip Code
  4.3.3. Compare the left most remaining three digits of the HIPAA Patient Zip Code to the HIPAA Zip Code Reference Table. If a match is found move "00000" to the HIPAA Patient Zip Code attribute
  4.3.4. Add 1 to the HIPAA Under 20K Zip counter within the Audit Encryption Counts table
Pass control to the Encrypt Data Attribute process

APPENDIX D

Data Supplier Encryption Function: Encrypt Data Attributes

| | |
|---|---|
| Summary | After the hipaatization process, attributes to be encrypted are passed to the encryption process. |
| Primary Actor(s) | HIPAA Privacy Compliance process (application process), Encrypt Data Attributes process (application process) |
| Secondary Actor(s) | Implementation Partner, Data Supplier |
| Pre-conditions | Data Attributes have been processed by the Standardize Data Attributes and HIPAA privacy compliance processes |
| Post-conditions | The input data attributes are encrypted. The encrypted attributes are available as output from the encryption process |
| Exceptions | No exception messages. All errors are recorded in the Audit Encryption Record counts Table |
| Dependent Use Case Description | 1. Process accepts attributes from the HIPAA Privacy Compliance Process
2. The following attributes will be encrypted
   Patient Data of Birth
   Cardholder Id
   Record Number (if requested)
   Patient Zip Code
   Patient First Name
   Patient Last Name
   NCPDP Patient Id
   Patient Street Address
3. To encrypt an attribute the application will
4. Acquire the attributes contents
   4.1. If the attribute's content is 'I' or 'B' (identified to be missing or invalid) move the contents directly into the corresponding encrypted attribute. Skip the remaining encryption steps for the attribute
   4.2. Acquire the encrypted Data Supplier Longitudinal Encryption Key 4.3. Decrypt the Data Supplier Longitudinal Encryption Key into its raw format
   4.4. Check for integrity of the Data Supplier Longitudinal Encryption Key. If the matching key is not found, the application will log an error and exit
   4.5. Encrypt the attributes contents using the Data Supplier Longitudinal Encryption Key (un-encrypted)
   4.6. Acquire the encrypted Data Supplier Encryption Key
   4.7. Decrypt the Data Supplier Encryption Key into its raw format
   4.8. Check for integrity of the Data Supplier Encryption Key. If the matching key is not found, the application will log an error and exit
   4.9. Encrypt the longitudinal encrypted results using the Data Supplier Encryption Key (un-encrypted)
   4.10. Repeat this step until all the input data attributes have been encrypted
5. After all attributes for a record have been encrypted add 1 to the Data Output Record count in the Audit Encryption Record Counts file |

APPENDIX E

Data Supplier Encryption Function: Request Audit Counts Reports

| | |
|---|---|
| Summary | The data encryption process creates audit counts for reporting/analysis. The reporting process, when requested, creates a report containing aggregated data encryption process audit counts |

APPENDIX E-continued

Data Supplier Encryption Function: Request Audit Counts Reports

| | |
|---|---|
| Primary Actor(s) | The operational process requesting a report |
| Secondary Actor(s) | Implementation Partner, Data Supplier |
| Pre-conditions | Data encryption application has processed creating audit counts for reporting/analysis<br>Report parameters have been defined |
| Post-conditions | Standard report of audit counts is produced for analysis |
| Exceptions | Default values used if input parameters are invalid |
| Dependent Use Case | |
| Description | Implementation Partner requests Audit Count information for analysis<br>User defines the execution parameters<br>1. Start Date (CCVYMMDD) - Audit information prior to the date specified will not be included. Defaults to current date minus one month<br>2. End Date (CCYYMMDD) - Audit information after the date specified will not be included. Defaults to current date<br>3. Aggregation Level<br>  3.1. Single (S) - Data aggregated by individual count into a single aggregated number (default).<br>    Aggregated counts for the entire time period<br>      2.3.2. By Day (D) - Data aggregated by unique date and present for each date encountered. Aggregated counts by day for the entire time period<br>  2.4. Reporting Option<br>    2.4.1. Print copy (P) - Results displayed in a report format for printing/faxing<br>    2.4.2. File copy (F) - Results written to a standard, predefined file location for further analysis j transmission (default). File format is identical to the Audit Encryption Counts table and enhance to hold potentially larger aggregated counts<br>  2.5. If any parameter is invalid the default value is used<br>User executes report |

APPENDIX F

LDF Encryption application Functions: Acquire Attributes

| | |
|---|---|
| Summary | This process will acquire attributes from the data supplier encryption process after the data feed split process. The split process will split the data supplier feed into transactional records and patient records. |
| Primary Actor(s) | LDF, Implementation Partner |
| Secondary Actor(s) | |
| Pre-conditions | New Data feed is available for processing at LDF |
| Post-conditions | |
| Exceptions | Error messages encountered will be written to the log file |
| Dependent Use Case | N/A |
| Description | The encryption application will process the configuration file and understand the list of attributes that will be encrypted. Refer Appendix A for LDF input file format.<br>The LDF encryption application should be able to handle the following scenarios<br>  1. Data file containing patient information.<br>  2. Data file containing limited patient information. |

APPENDIX G

LDF Encryption Function: LDF Data Encryption

| | |
|---|---|
| Summary | The encryption application will decrypt the records received after the acquire attribute process using the data supplier longitudinal key followed by encryption using the LDF longitudinal key. |

APPENDIX G-continued

LDF Encryption Function: LDF Data Encryption

| | |
|---|---|
| Primary Actor(s) | Encryption Application (application process), Hardware Security Module (nCipher) |
| Secondary Actor(s) | Implementation Partner |
| Pre-conditions | 1. Encrypted Attributes are identified and separated before passing it on the encryption application. (Scope of implementation partner).<br>2. Data Supplier encryption key, LDF Longitudinal Encryption Key and the LDF Data Encryption software has been successfully installed and secured in a restricted access environment managed by the<br>3. Execution Type parameter set prior to execution.<br>4. Attribute mapping of the encrypted attributes on the input file have been set-up. |
| Trigger | File containing all encrypted attributes have been identified and separated. |
| Pot-conditions | None |
| Frequency | Agreed upon between LDF and Data Supplier |
| Exceptions | Exception message 1 if the file is not complete.<br>All errors are recorded in the Audit Encryption Record counts Table |
| Special Requirements | The matching attribute in the data file will serve as a link to the corresponding health care records.<br>It will be passed through the.<br>process and remain linked to the individual transaction information.<br>The encryption application runs in a secure isolated hardware platform to which only the implementation partner and the key administrator have access.<br>Audit counts containing the number of encrypted records |
| Description | Encryption application process accepts records once they are identified and separated. The attributes that need to be decrypted are<br>  Patient Data of Birth<br>  Cardholder Id<br>  Record Number<br>  Patient Zip Code<br>  Patient First Name<br>  Patient Last Name<br>  Patient Id<br>  Patient Street Address<br>The process will accept the Execution Type parameter.<br>2.1. The valid execution types will be<br>    2.1.1. Blank - routine execution<br>    2.1.2. R - Re-execution due to processing error<br>    2.1.3. D - Process identified the current feed to be a duplicate of one already processed<br>Within the hardware security module:<br>3.1. Extract and decrypt the data supplier encryption key and the LDF longitudinal key from the hardware security module and load it in secure access area.<br>3.2. For each encrypted record received<br>    3.2.1. Add one to the LDF Data Encryption Record Received count for the identified data supplier.<br>    3.2.2. Each time a new Supplier Number/Data Supplier Processing Date is encountered a new LDF Audit Encryption count record is written to the secure and non-secure file.<br>      3.2.2.1. The Supplier number is populated with the Supplier Number on the Encrypted data record<br>      3.2.2.2. The Data Supplier's Processing Date is populated with the Data Supplier's Processing date received.<br>      3.2.2.3. The LDF Processing Date is populated with the current system date<br>      3.2.2.4. Populate Execution type field as appropriate.<br>      3.2.2.5. All other count fields are initialized to zero<br>3.3. Extract attribute by attribute from the file.<br>3.4. Application will validate each encrypted attribute to match the size/data type as expected (from the Data Supplier Encryption application). Validation includes:<br>    3.4.1. Proper length<br>    3.4.2. Attributes are fully populated |

APPENDIX G-continued

LDF Encryption Function: LDF Data Encryption 3.4.3. Attributes are populated with a encrypted code or populated with 'I' or 'B' (invalid or missing data submitted)
  3.4.4. If the encrypted data attributes are not properly formatted exception message 1 will be displayed and the process is terminated (until the input file errors can be resolved)
 3.5. Perform decryption on the data attribute using the data supplier encryption key
  3.5.1. Determine if the attribute can be decrypted. If yes perform decryption.
  3.5.2. Attributes populated with 'I' or '8' (invalid or missing data submitted) will not be decrypted
 3.6. For each record decrypted add 1 to the Attribute Unencrypted Count field within the LDF Audit Encryption Counts file 3.7. Encrypt the attribute using the LDF longitudinal key.
 3.8. Attributes populated with 'I' or 'B' (invalid or missing data submitted) will not be encrypted
 3.9. Add 1 to the Attribute LDF Encrypted Count field within the LDF Audit Encryption Counts file.
 3.10. Write the re-encrypted record to the LDF Encrypted Record file/table For each record encrypted add 1 to the Record Release Count field within the LDF Audit Encryption Counts file/table.
 3.11. On completion of decryption destroy data supplier encryption key and the LDF longitudinal key from the memory space of the Hardware Security Module.
 3.12. Record is passed into the LDF Data Encryption Process

APPENDIX H

LDF Encryption Application Function: LDF Audit Count Reporting

| | |
|---|---|
| Summary | This use describes the process of generating reports from both secure and non-secure logs |
| Primary Actor | Implementation Partner |
| Secondary Actor(s) | None |
| Pre-conditions | LDF data encryption application has processed creating audit counts for reporting/analysis Report execution parameters have been set-up |
| Trigger | None |
| Post-conditions | Standard report of audit counts produced for analysis |
| Frequency | Not Applicable |
| Exceptions | Default values used if input parameters are invalid |
| Special Requirements | None |
| Description | 1. Implementation Partner requests Audit Count information for analysis
2. User defines the execution parameters
2.1. Date to be utilized - User specifies whether to use the data supplier processing date or the LDF processing date.
2.2. Start Date (CCVYMMDD) - Audit information prior to the date specified will not be included. Defaults to current date minus one month.
2.3. End Date (CCVYMMDD) - Audit information after the date specified will not be included. Defaults to current date. The end date can be either a data supplier processing date or the LDF encryption application processing date
2.4. Data Supplier - Data supplier id to execute report against. Blank assumes all data suppliers (default)
2.5. Aggregation Level
2.5.1. Single (S) - Data aggregated by data supplier by unique count into a single aggregated number (default)
2.5.2. By Day (D) - Data aggregated by data supplier by unique date and present for each date encountered
2.6. Reporting Option
2.6.1. Print copy (P) - Results displayed in a report format for printing / faxing |

APPENDIX H-continued

LDF Encryption Application Function: LDF Audit Count Reporting

| | |
|---|---|
| | 2.6.2. File copy (F) - Results written to a standard, predefined file location for further analysis/transmission (default). File format is identical to the Audit Encryption Counts table and enhance to hold potentially larger aggregated counts
2.7. If any parameter is invalid the default value is used 3. User executes report
3. User executes report |
| Reports | Audit Data Encryption Report |

APPENDIX I

Key Administrator Function: Generate Encryption Keys

| | |
|---|---|
| Summary | The key administrator serves as a trusted third party and generates various encryption keys for use at the data supplier and LDF ends. |
| Primary Actor | Key generation process |
| Secondary Actor(s) | Key Administrator |
| Pre-conditions | The key generation application has been installed at the key administrator's end |
| Post-conditions | A 128-bit encryption key is generated |
| Exceptions | |
| Dependent Use Case | |
| Description | 1. The key administrator invokes the key generation process
1.1. A unique 128-bit encryption key is generated
2. After generation of the key, the process invokes the key storage process for securing the key that is generated
3. The key is encrypted for distribution (compliant with the expectations of the Data Supplier encryption application and the LDF encryption application) |

APPENDIX J

Other Function: Secure key storage

| | |
|---|---|
| Summary | The encryption keys, LDF Longitudinal Key and Data Supplier Encryption Key, should be stored securely. For secure storage of these keys, the keys are stored in an encrypted form. The password for decryption of the keys is known j can be derived only by the application. |
| Primary Actor | The application process that implements secure key storage |
| Secondary Actor(s) | Key Administrator, Implementation Partner, Data Supplier |
| Pre-conditions | 1. At the key administrator end, the Key Administrator has generated the encryption keys using the key generation process and encrypted them.
2. At the data supplier end, the Key Administrator has securely communicated the encrypted LDF Longitudinal Key and Data Supplier Encryption Key to the Implementation Partner at the data supplier end |
| Post-conditions | The key generated using the key generation process is encrypted |
| Exceptions | |
| Dependent Use Case | |
| Description | 1. The password for encryption of the encryption keys is buried into/derived by the secure key storage logic
2. The encryption keys are encrypted using the password got from the above step |

APPENDIX K

| | Other Function: Secure audit storage |
|---|---|
| Summary | The integrity of the audit counts produced by the standardization and encryption process will have to be preserved at both the data supplier end and LDF end |
| Primary Actor | The application process that implements secure audit storage |
| Secondary Actor(s) | Implementation Partner, Data Supplier, LDF |
| Pre-conditions | The audit counts are produced by the encryption and standardization processes |
| Post-conditions | The audit is secured by preserving its integrity |
| Exceptions | |
| Dependent Use Case | |
| Description | 1. Process reads the audit counts file<br>2. Process ensures integrity of the audit counts file, say by calculating a checksum over the file |

We claim:

1. A method for assembling a longitudinally-linked database from individual patient healthcare transaction data records, the method comprising:
at a central facility (LDF),
receiving data records including at least one patient non-identifying attribute and at least one individually encrypted patient-identifying attribute, the at least one patient-identifying attribute first encrypted using a first encryption key specific to the LDF and further encrypted with a second encryption key unique to a data source so that original unencrypted patient identification information in the at least one patient-identifying attribute remains secret with respect to other data sources;
partially decrypting the received data records using a decryption key complementary to the second encryption key so that the at least one patient-identifying attribute retains only the encryption by the first encryption key specific to the LDF;
using an attribute-matching algorithm to assign an LDF identifier (ID) to the encrypted data records; and
linking the encrypted data records ID by ID, whereby the longitudinally-linked data base is formed.

2. The method of claim 1 wherein the at least one patient-identifying attribute is encrypted using a third encryption key specific to the LDF.

3. The method of claim 1 wherein the acquired data records are processed to place their data fields in a standard content format.

4. The method of claim 1 wherein the at least one patient-identifying attribute and the at least one patient non-identifying attribute are separated in the data records, and the separated at least one patient-identifying attribute is encrypted.

5. The method of claim 4 wherein the encrypted at least one patient-identifying attribute is merged with the separated at least one non-identifying attribute in the data records.

6. The method of claim 1 further comprising processing the received data records to separate the at least one encrypted patient-identifying attribute and the at least one non-identifying attribute in the data records, and partially decrypting the separated at least one patient-identifying attribute.

7. The method of claim 6 further comprising merging the at least one partially decrypted patient-identifying attribute with the at least one separated non-identifying attribute in the data records.

8. The method of claim 1 wherein the attribute-matching algorithm assigns an ID to an encrypted data record based on a statistical match of a select set of data attributes.

9. The method of claim 8 wherein the select set of data attributes comprises at least one of a patient's date of birth, cardholder identification, record number, zip code, first name, last name, street address, and an industry standard patient identifier.

10. The method of claim 1 wherein the attribute-matching algorithm assigns an ID to an encrypted data record by referencing a cross database of IDs and corresponding attributes.

11. The method of claim 1 wherein the receiving the data records and the partially decrypting are performed in a secure environment that limits unauthorized access to patient-identifying attribute information in the data records.

12. A system for longitudinally-linking individual patient healthcare transaction data records obtained from multiple data suppliers, the system comprising:
at a central facility (LDF), a first component configured to:
receive data records including at least one patient non-identifying attribute and at least one individually, doubly encrypted patient-identifying attribute encrypted with a first encryption key specific to an LDF and further encrypted with a second encryption key unique to a data source so that original unencrypted patient identification information in the at least one patient-identifying attribute remains secret with respect to other data sources;
partially decrypt the received data records using a decryption key complementary to the second encryption key so that the at least one patient-identifying attribute retains the encryption by the first encryption key specific to the LDF;
perform an additional layer of encryption on the data records; and
a second component configured to:
assign an LDF identifier (ID) to the encrypted data records by matching attributes in the encrypted data records; and
link the encrypted data records ID by ID, whereby a longitudinal database is formed.

13. The system of claim 12 wherein the at least one patient-identifying attribute and the at least one patient non-identifying attribute in the data records are separated and the separated at least one patient-identifying attribute is encrypted.

14. The system of claim 13 wherein the encrypted at least one patient-identifying attribute is merged with the separated at least one patient non-identifying attribute in the data records.

15. The system of claim 12 wherein the acquired data records are processed to place their data fields in a standard format.

16. The system of claim 12 wherein the first component is further configured to separate the encrypted at least one patient-identifying attribute and the at least one non-identifying attribute in the received data records, and to partially decrypt the separated at least one patient-identifying attribute.

17. The system of claim 16 wherein the first component is further configured to merge the at least one partially decrypted patient-identifying attribute with the separated at least one non-identifying attribute in the data records.

18. The system of claim 12 wherein the second component is further configured to assign an LDF identifier (ID) to the encrypted data records based on a statistical match of a select set of data attributes.

19. The system of claim 18 wherein the select set of data attributes comprises at least one of a patient's date of birth, cardholder identification, record number, zip code, first name, last name, street address, and an industry standard patient identifier.

20. The system of claim 18 wherein the second component is further configured to assign an LDF identifier (LI) to the encrypted data records by referencing a cross database of LIs and corresponding attributes.

21. The system of claim 12 wherein the first component is configured for operation in a secure environment that limits unauthorized access to patient-identifying attribute information in the data records.

22. The system of claim 12 whose functions are implemented using software applications.

23. A longitudinally-linked electronic database assembled from individual patient healthcare transaction data records, the electronic database comprising:

multi-sourced data records in which patient identifying attributes are encrypted to preserve patient privacy, wherein each encrypted data record is assigned an identifier based on a statistical match of a select set of data attributes with a reference set of values, wherein the data records are linked by the assigned identifiers wherein, when received, the patient-identifying attributes are doubly encrypted on an individual attribute basis with a first encryption key specific to a central facility (LDF) and a second encryption key specific to a data supplier so that original unencrypted patient identification information in the patient-identifying attributes remains secret with respect to other data suppliers and wherein the electronic database is coupled to a hardware security module comprising an encryption application programmed to partially decrypt the received attributes using a decryption key complementary to the second encryption key so that the attributes retain only the encryption by the first encryption key specific to the LDF.

24. The longitudinally-linked electronic database of claim 23, wherein the select set of data attributes comprises at least one of a patient's date of birth, cardholder identification, record number, zip code, first name, last name, street address, and an industry standard patient identifier.

* * * * *